United States Patent
Lin et al.

(10) Patent No.: US 11,338,051 B2
(45) Date of Patent: May 24, 2022

(54) CLOSURE MECHANISMS AND SEAL INTEGRITY INDICATORS FOR STERILIZATION CONTAINERS

(71) Applicant: O&M Halyard, Inc., Mechanicsville, VA (US)

(72) Inventors: Brian E. Lin, Cumming, GA (US); Joseph D. Hurdle, Canton, GA (US); Sharon Shuh-Shin Chang, Alpharetta, GA (US); Anthony Stephen Spencer, Woodstock, GA (US); Prasad Shrikrishna Potnis, Johns Creek, GA (US)

(73) Assignee: O&M Haylard, Inc., Mechanicsville, VA (US)

( * ) Notice: Subject to any disclaimer, the term of this patent is extended or adjusted under 35 U.S.C. 154(b) by 289 days.

(21) Appl. No.: 16/524,711

(22) Filed: Jul. 29, 2019

(65) Prior Publication Data
US 2020/0147250 A1    May 14, 2020

Related U.S. Application Data

(60) Provisional application No. 62/757,852, filed on Nov. 9, 2018.

(51) Int. Cl.
*A61L 2/26* (2006.01)
*A61L 2/07* (2006.01)
(Continued)

(52) U.S. Cl.
CPC ............... *A61L 2/26* (2013.01); *A61L 2/07* (2013.01); *A61L 2/14* (2013.01); *A61L 2/206* (2013.01);
(Continued)

(58) Field of Classification Search
None
See application file for complete search history.

(56) References Cited

U.S. PATENT DOCUMENTS 3,527,400 A    9/1970  Shepherd et al.
3,730,338 A    5/1973  Chesky
(Continued)

FOREIGN PATENT DOCUMENTS

CN    103480022 A    1/2014
JP    2005230436 A    9/2005
(Continued)

*Primary Examiner* — Holly Kipouros
(74) *Attorney, Agent, or Firm* — Dority & Manning, P.A.

(57) ABSTRACT

Closure mechanisms for closing and sealing sterilization containers and indicators for indicating the seal integrity sterilization containers are provided. For example, a container closure mechanism may be configured to distribute a closure force along a gasket to seal a container lid to a container body. Further, a seal indicator may visibly indicate at the container exterior whether the container is sufficiently sealed to prevent an ingress of contaminants into the container. If the container is sufficiently sealed, the seal indicator is a first state, and if the sterilization container is not sufficiently sealed, the seal indicator is in a second state. Thus, the seal indicator undergoes a state change when the sterilization container transitions from unsealed to sealed or from sealed to unsealed, such that a user can ascertain whether the container is properly sealed to maintain sterility or whether the seal and sterility of the container have been compromised.

14 Claims, 14 Drawing Sheets

(51) Int. Cl.
*A61L 2/14* (2006.01)
*A61L 2/20* (2006.01)
*A61B 50/30* (2016.01)

(52) U.S. Cl.
CPC ......... *A61L 2/208* (2013.01); *A61L 2202/121* (2013.01); *A61L 2202/122* (2013.01); *A61L 2202/182* (2013.01); *A61L 2202/24* (2013.01)

(56) References Cited

U.S. PATENT DOCUMENTS

| | | | |
|---|---|---|---|
| 4,193,496 A | 3/1980 | Barratt | |
| 4,349,118 A | 9/1982 | Sanderson et al. | |
| 4,466,552 A | 8/1984 | Butterworth et al. | |
| 4,489,841 A | 12/1984 | Thompson | |
| 4,551,311 A | 11/1985 | Lorenz | |
| 4,562,047 A | 12/1985 | Sestak et al. | |
| 4,643,303 A | 2/1987 | Arp et al. | |
| 4,671,943 A | 6/1987 | Wahlquist | |
| 4,706,839 A | 11/1987 | Spence | |
| 4,774,063 A | 9/1988 | Runnells | |
| 4,915,913 A | 4/1990 | Williams et al. | |
| 4,919,888 A | 4/1990 | Spence | |
| 5,115,929 A | 5/1992 | Buono | |
| 5,147,351 A | 9/1992 | Wagner | |
| 5,217,698 A | 6/1993 | Siegel et al. | |
| 5,372,787 A | 12/1994 | Ritter | |
| 5,407,069 A | 4/1995 | Schmieding et al. | |
| 5,427,266 A | 6/1995 | Yun | |
| 5,573,741 A | 11/1996 | Riley | |
| 5,641,065 A | 6/1997 | Owens et al. | |
| 5,887,745 A * | 3/1999 | Wood | B65D 45/18 220/326 |
| 6,010,670 A | 1/2000 | Berry, Jr. | |
| 6,099,812 A | 8/2000 | Allen et al. | |
| 6,189,551 B1 | 2/2001 | Sargent et al. | |
| 6,207,100 B1 | 3/2001 | Weiss et al. | |
| 6,247,609 B1 | 6/2001 | Gabele et al. | |
| 6,311,838 B1 | 11/2001 | Johnson et al. | |
| 6,350,418 B1 | 2/2002 | Venderpool et al. | |
| 6,589,477 B1 | 7/2003 | Frieze et al. | |
| 6,669,360 B1 | 12/2003 | Adelmann et al. | |
| 6,755,207 B1 | 6/2004 | Curtis et al. | |
| 6,880,869 B2 * | 4/2005 | Schainholz | A61L 2/28 292/307 A |
| 6,893,158 B1 | 5/2005 | Tipp et al. | |
| 7,106,202 B2 | 9/2006 | Dickinson | |
| 8,435,445 B2 | 5/2013 | Kral | |
| 8,623,289 B2 | 1/2014 | Cesa et al. | |
| 8,763,839 B2 | 7/2014 | Sakairi | |
| 8,815,174 B2 | 8/2014 | Bacik et al. | |
| 8,899,443 B2 | 12/2014 | Soibel et al. | |
| 9,028,147 B2 | 5/2015 | Schmal et al. | |
| 9,111,425 B2 | 8/2015 | Holloway et al. | |
| 9,125,727 B2 | 9/2015 | Dallafior | |
| 9,572,905 B2 | 2/2017 | Schulz et al. | |
| 9,610,126 B2 | 4/2017 | Griffin | |
| 2001/0032850 A1 | 10/2001 | Neuner | |
| 2004/0197248 A1 | 10/2004 | Hasegawa et al. | |
| 2006/0000733 A1 | 1/2006 | Albritton et al. | |
| 2009/0266818 A1 | 10/2009 | Sauvageau | |
| 2010/0258493 A1 * | 10/2010 | Kindkeppel | B01D 29/01 210/235 |
| 2012/0152957 A1 * | 6/2012 | Smith | A61L 2/26 220/495.01 |
| 2012/0211493 A1 | 8/2012 | Daggett | |
| 2013/0171030 A1 * | 7/2013 | Ferlic | A61L 2/18 422/119 |
| 2013/0280134 A1 | 10/2013 | Hoffman et al. | |
| 2015/0327934 A1 | 11/2015 | Thomas et al. | |
| 2015/0368009 A1 | 12/2015 | Loukov | |
| 2016/0083150 A1 | 3/2016 | Diminick et al. | |
| 2016/0108566 A1 | 4/2016 | Tseng et al. | |
| 2016/0194126 A1 | 7/2016 | Findlay | |
| 2016/0263264 A1 | 9/2016 | Schulz et al. | |
| 2017/0239381 A1 * | 8/2017 | Cohen | A61L 2/07 |
| 2018/0105334 A1 | 4/2018 | Carver et al. | |
| 2020/0114032 A1 * | 4/2020 | Spencer | A61B 50/00 |

FOREIGN PATENT DOCUMENTS

| | | |
|---|---|---|
| WO | WO 2008/078169 A2 | 7/2008 |
| WO | WO 2015/017828 A1 | 2/2015 |
| WO | WO 2019/006079 A2 | 1/2019 |

* cited by examiner

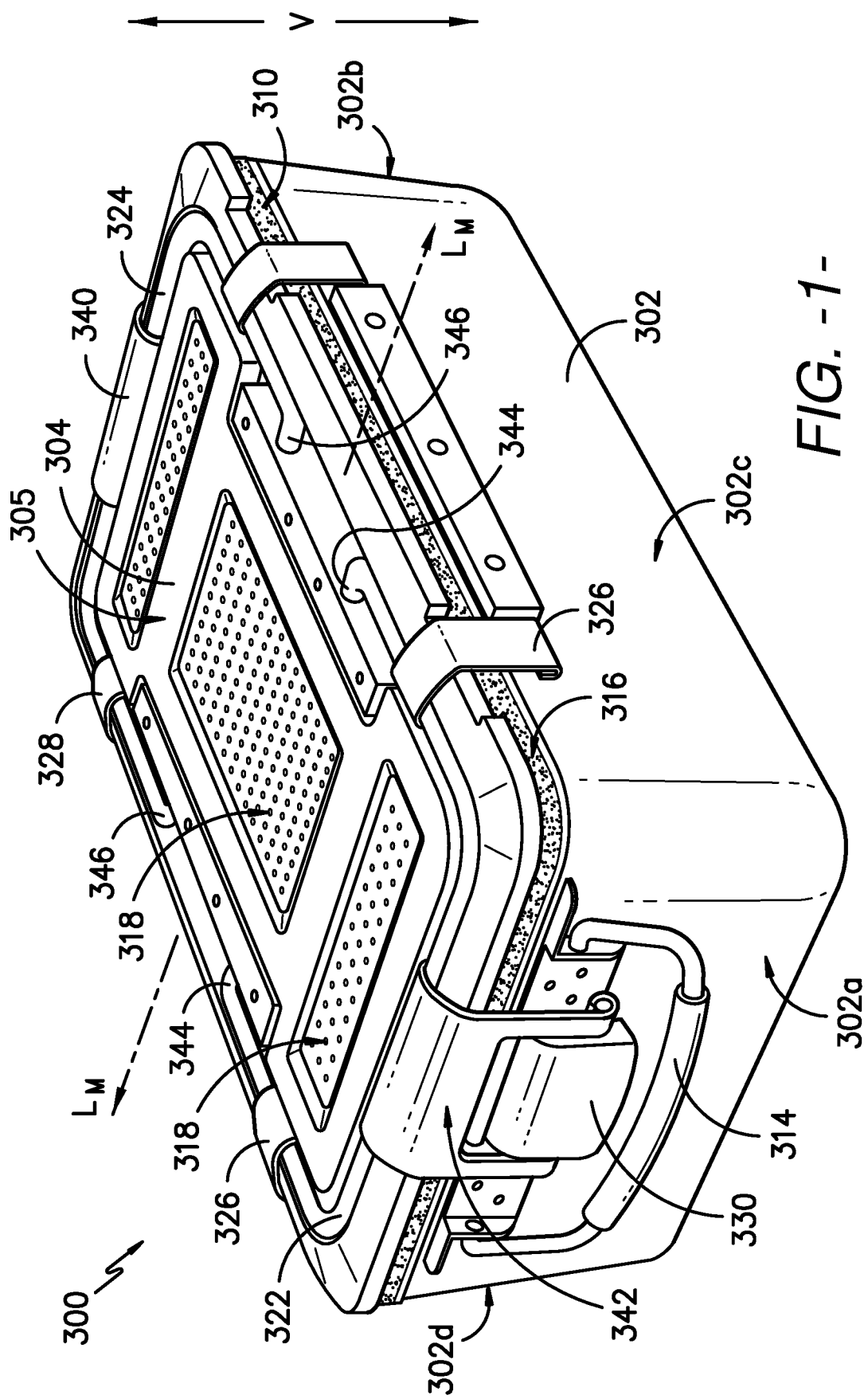
FIG. -1-

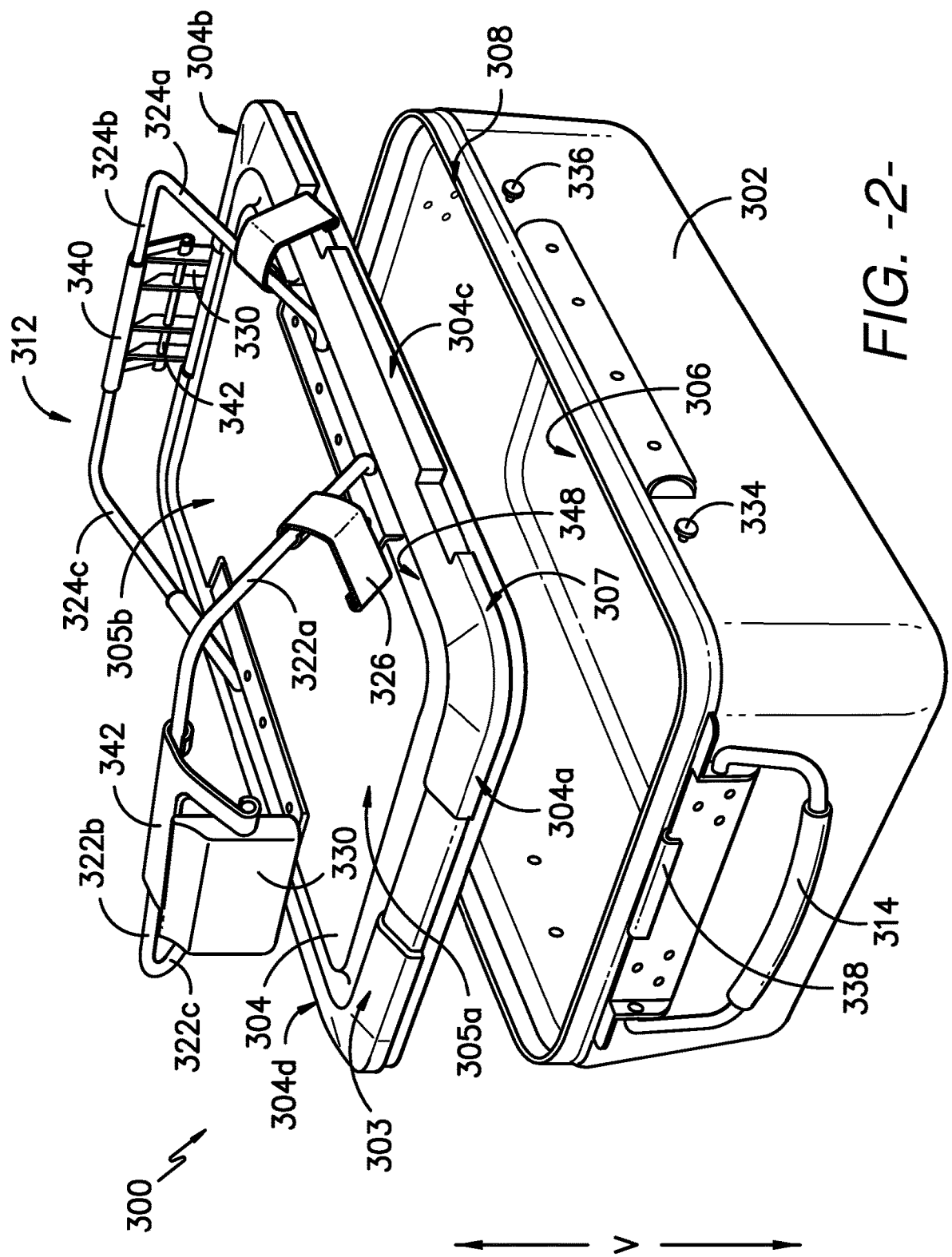
FIG. -2-

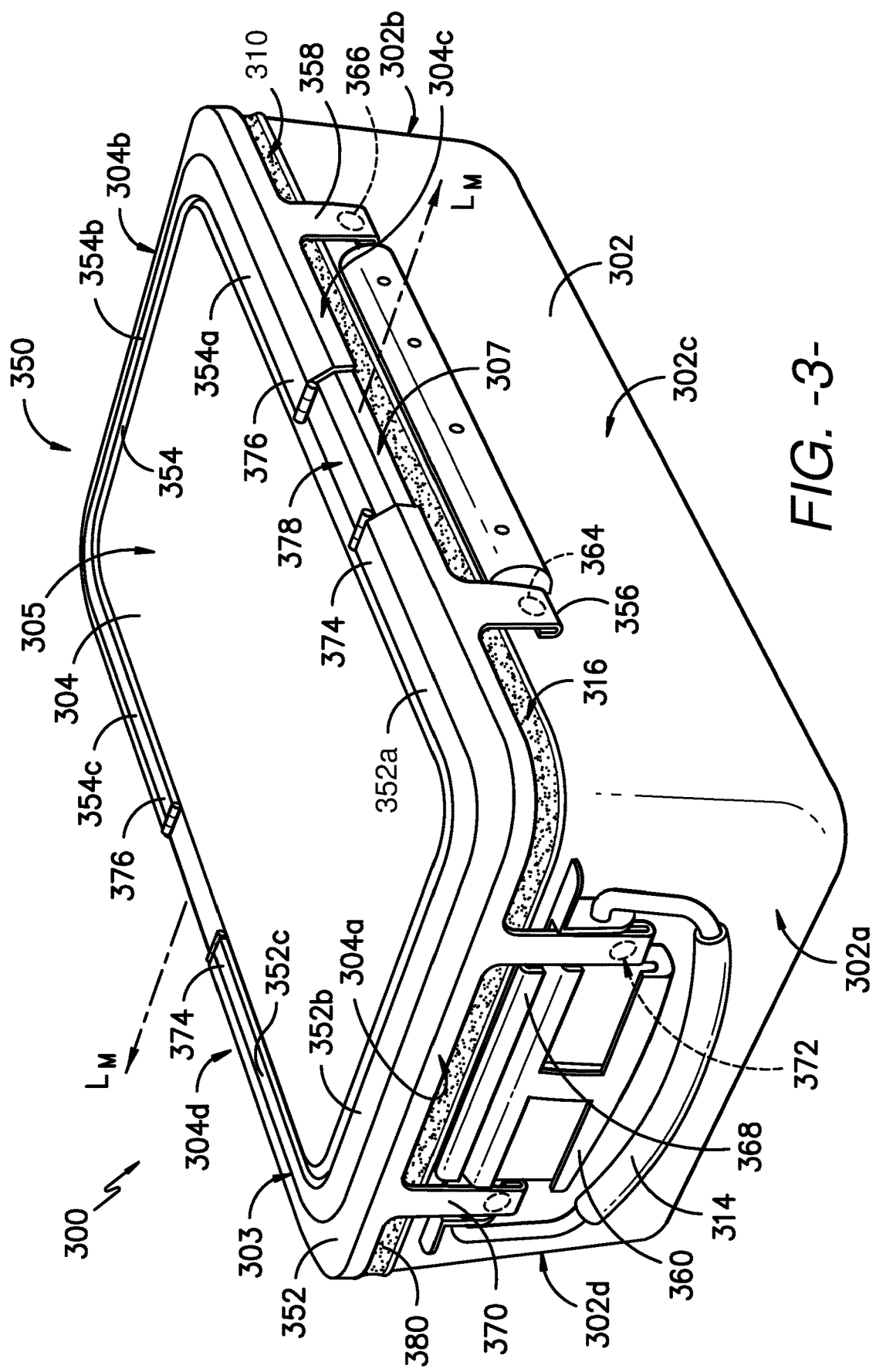
FIG. -3-

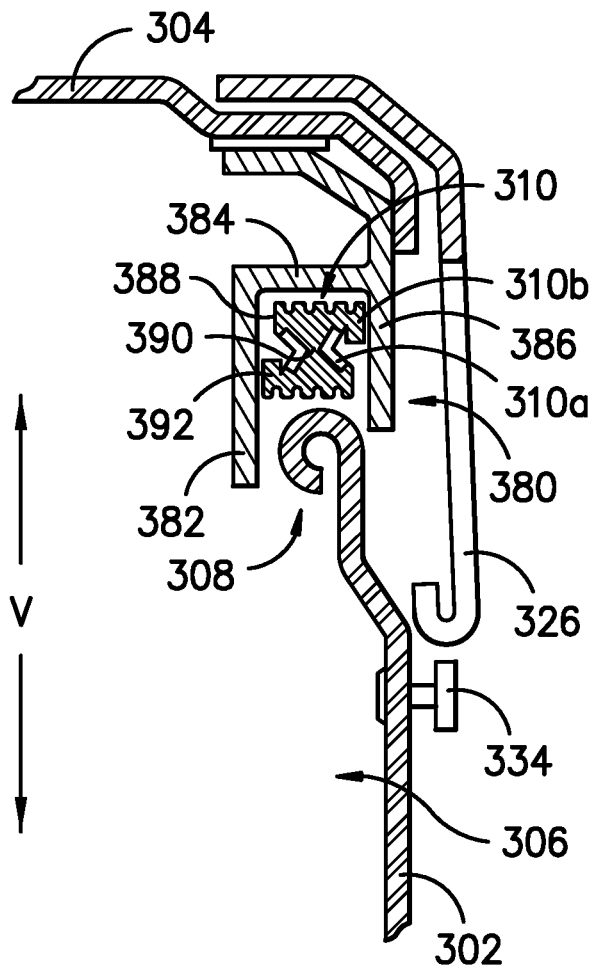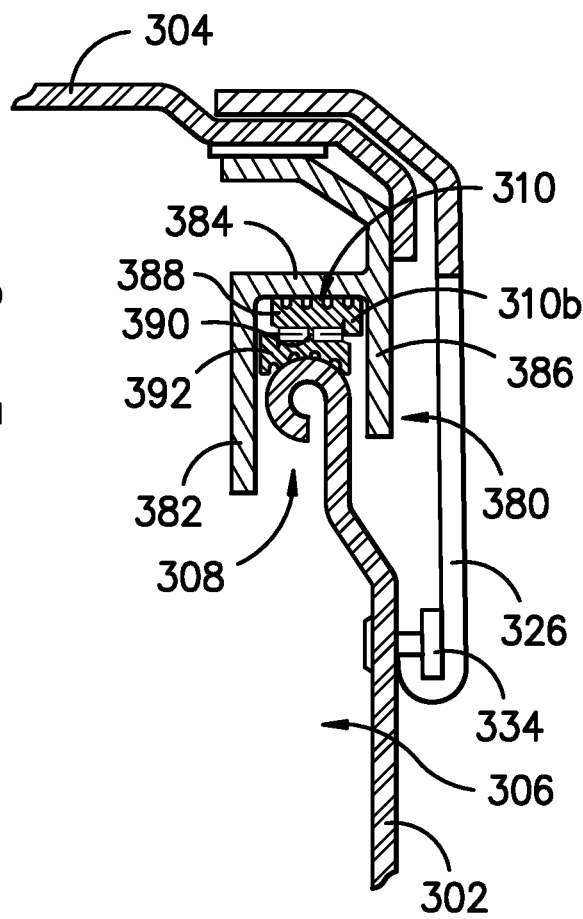
FIG. -4-  FIG. -5-

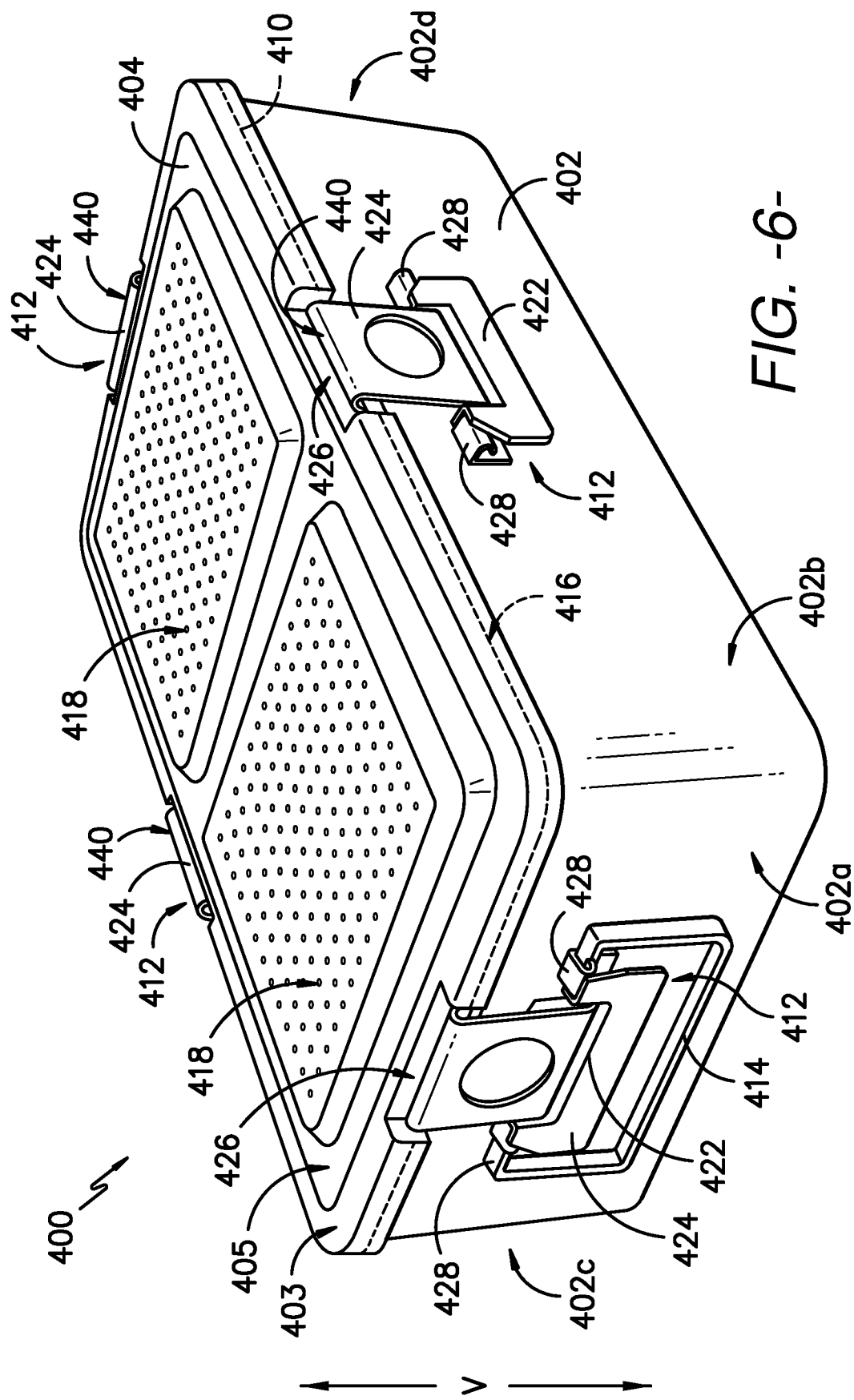
FIG. -6-

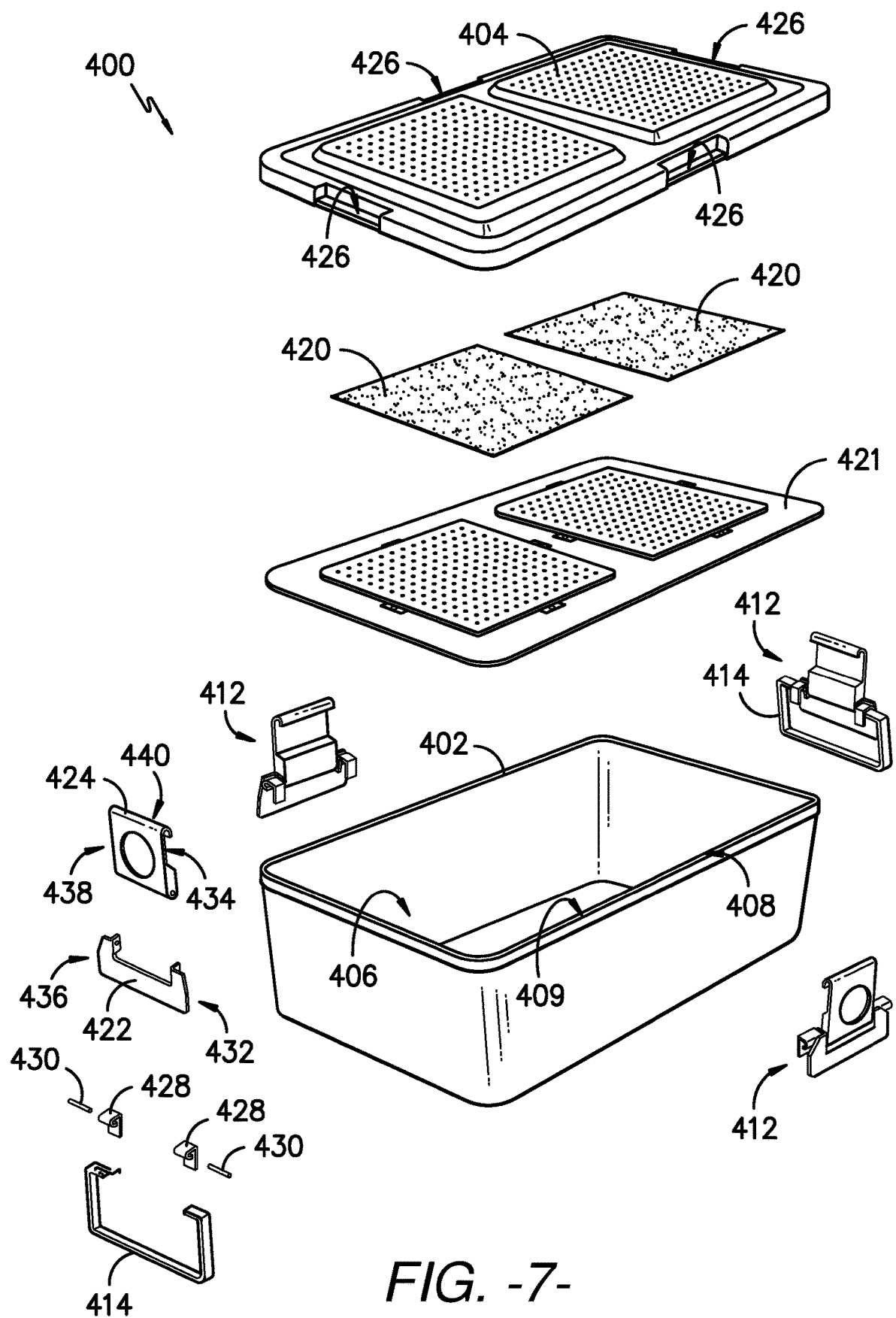
FIG. -7-

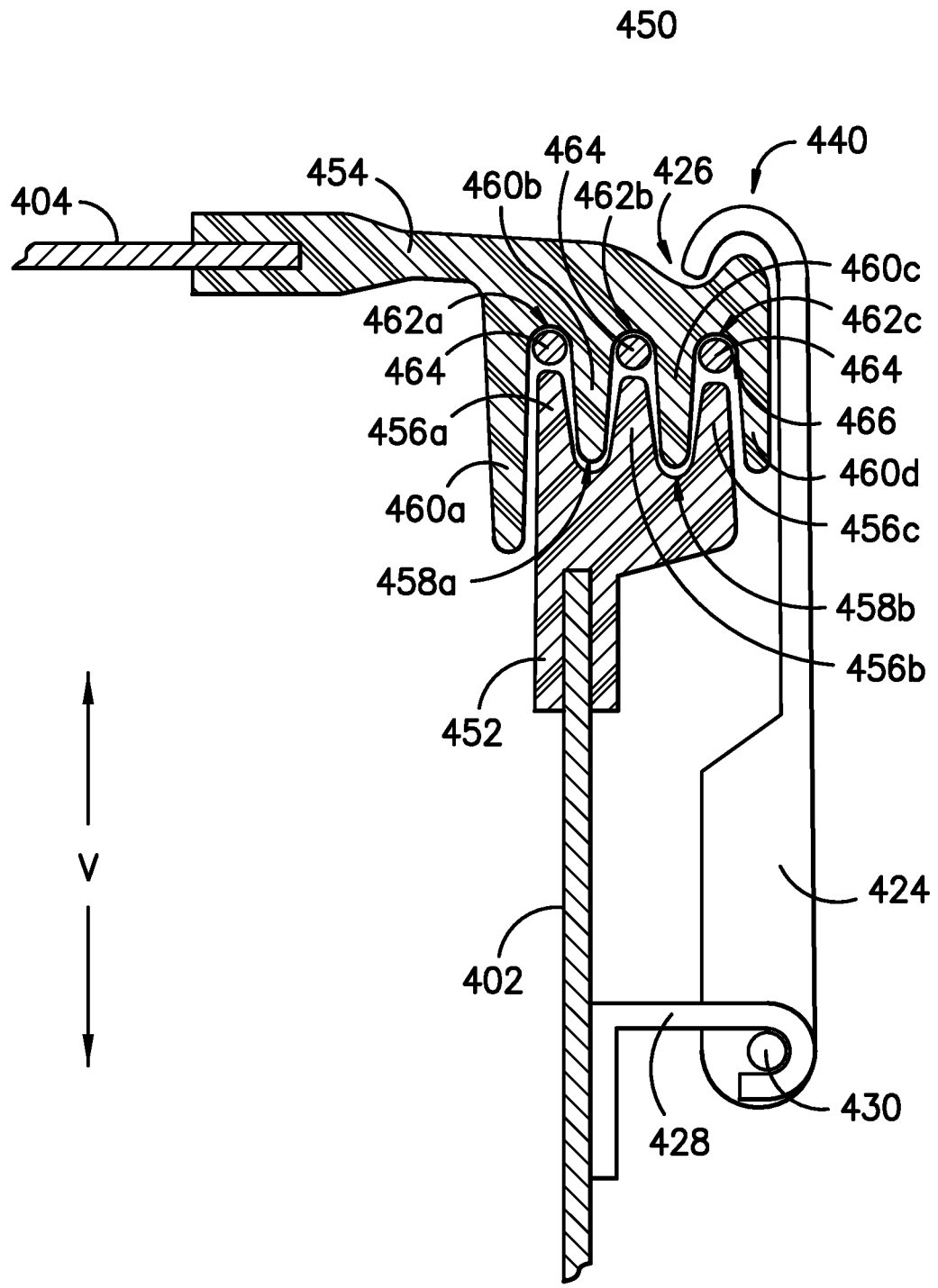
FIG. -8-

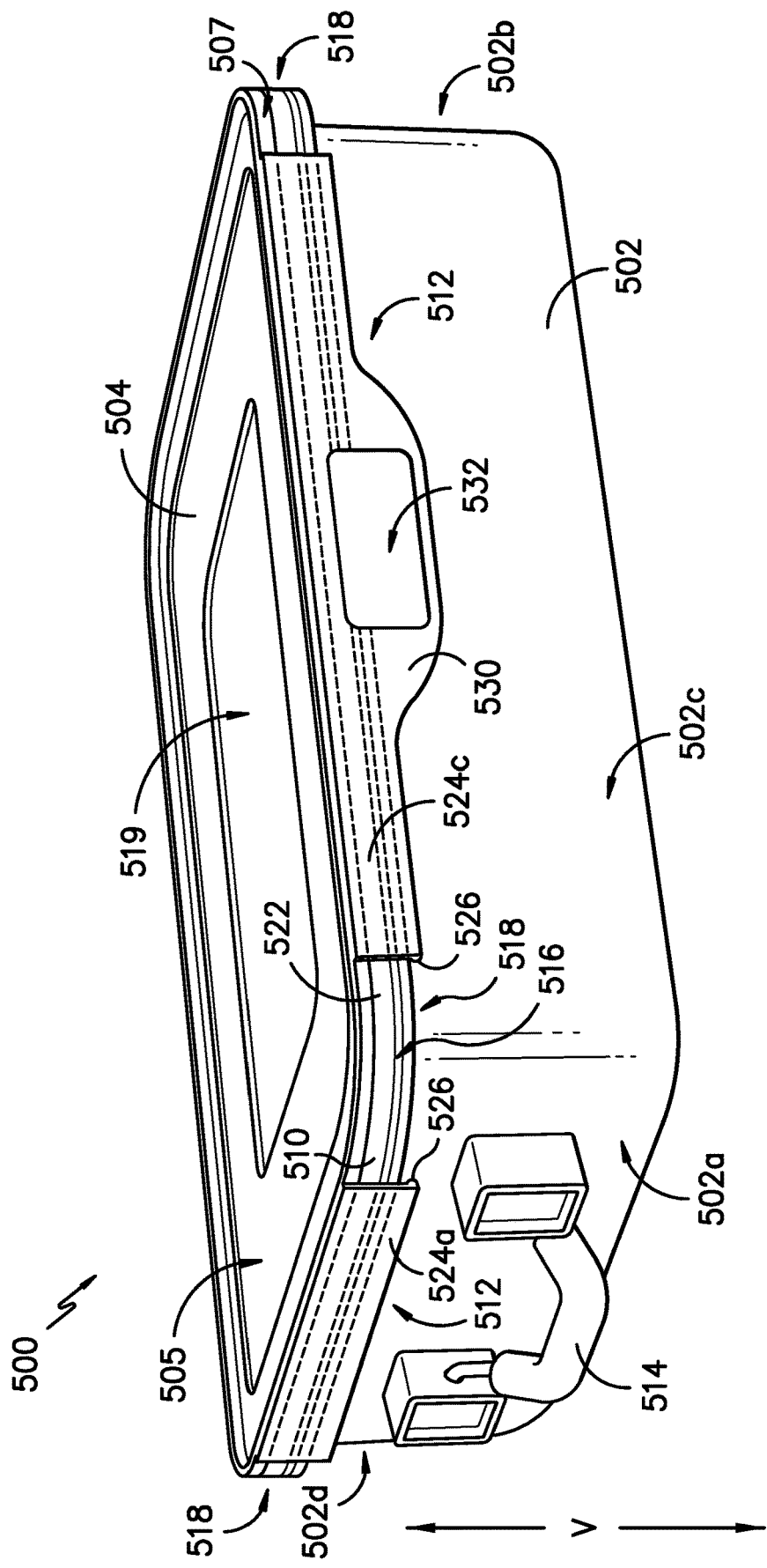
FIG. -9-

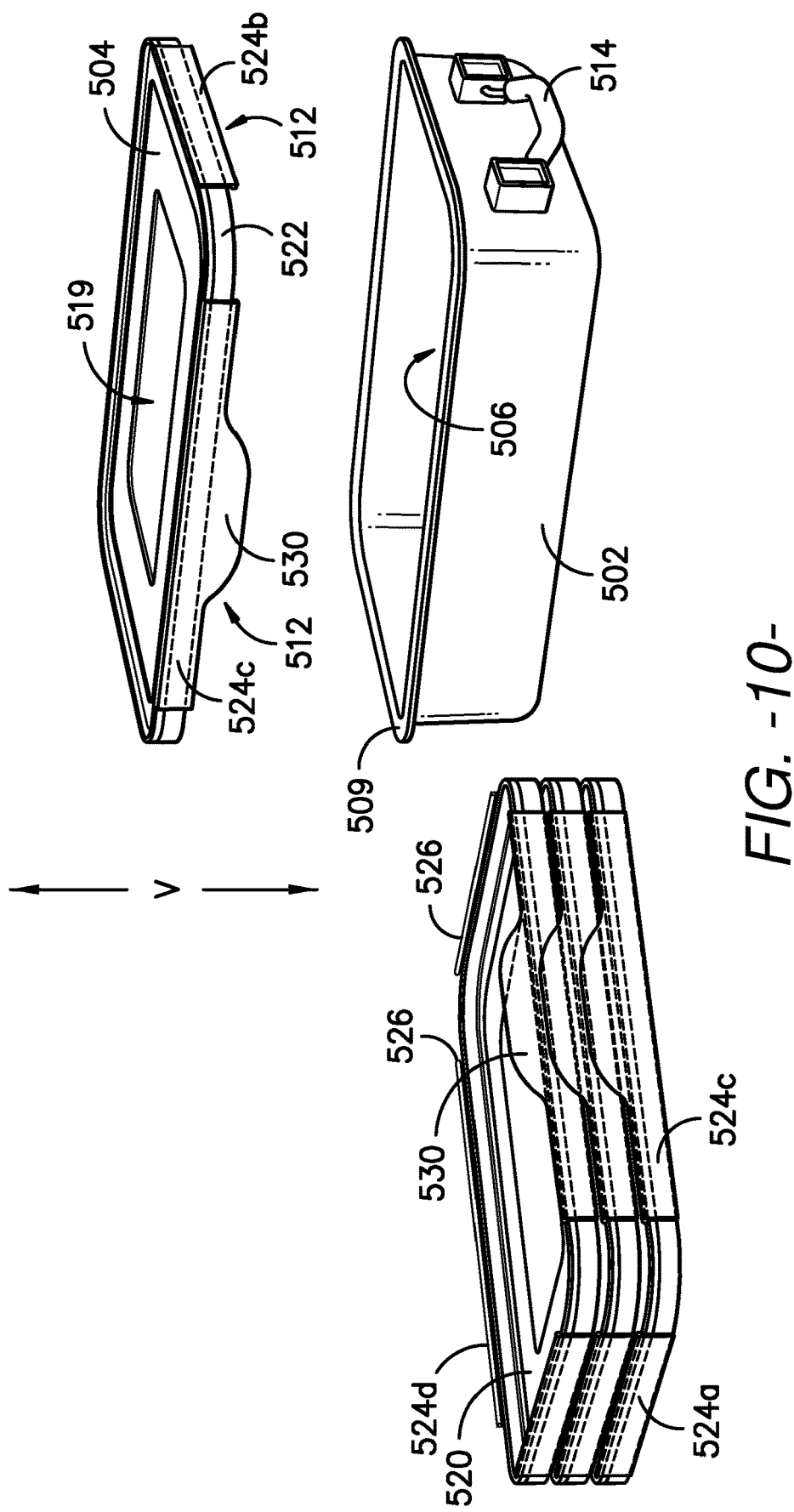
FIG. -10-

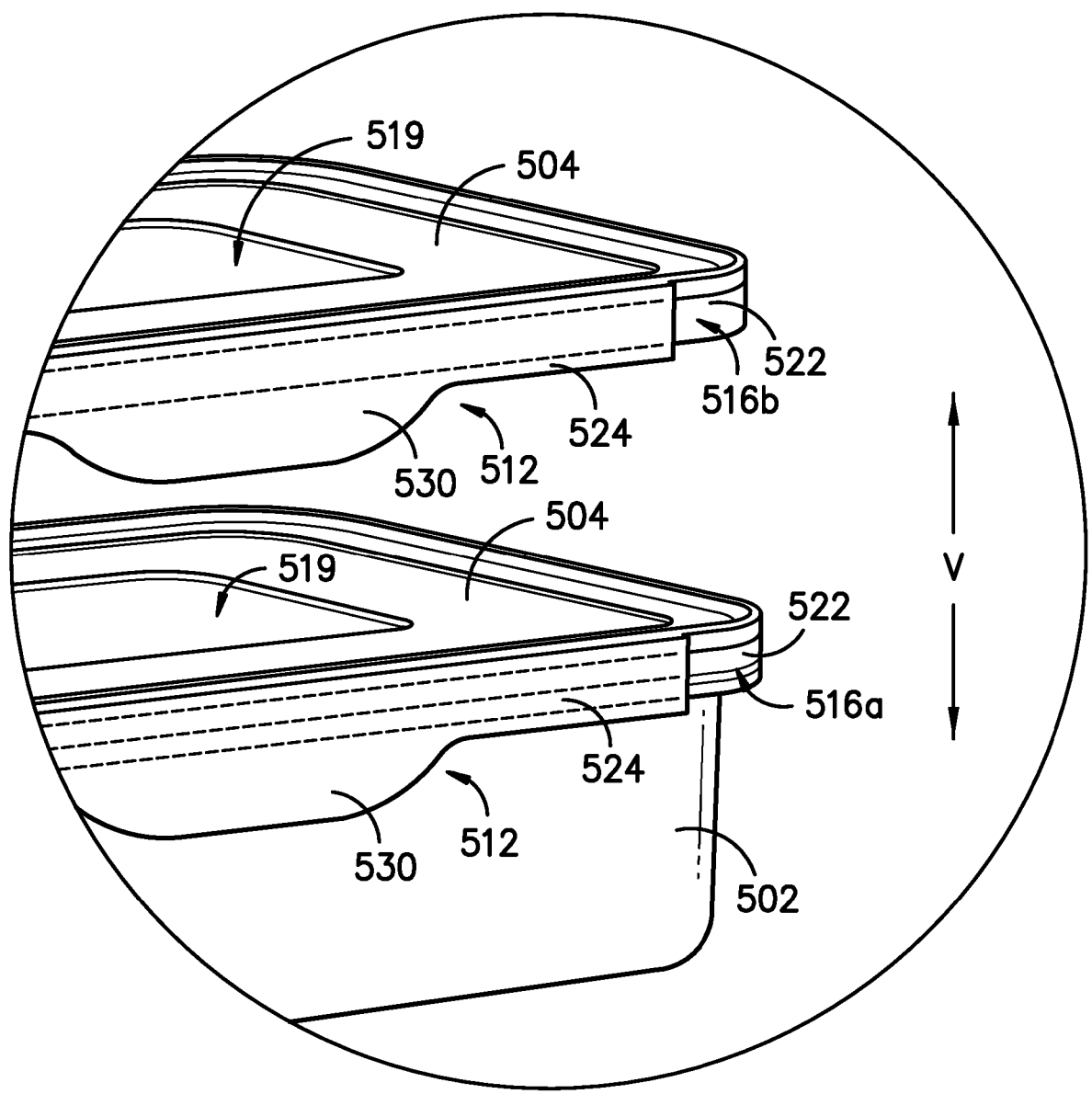
FIG. -11-

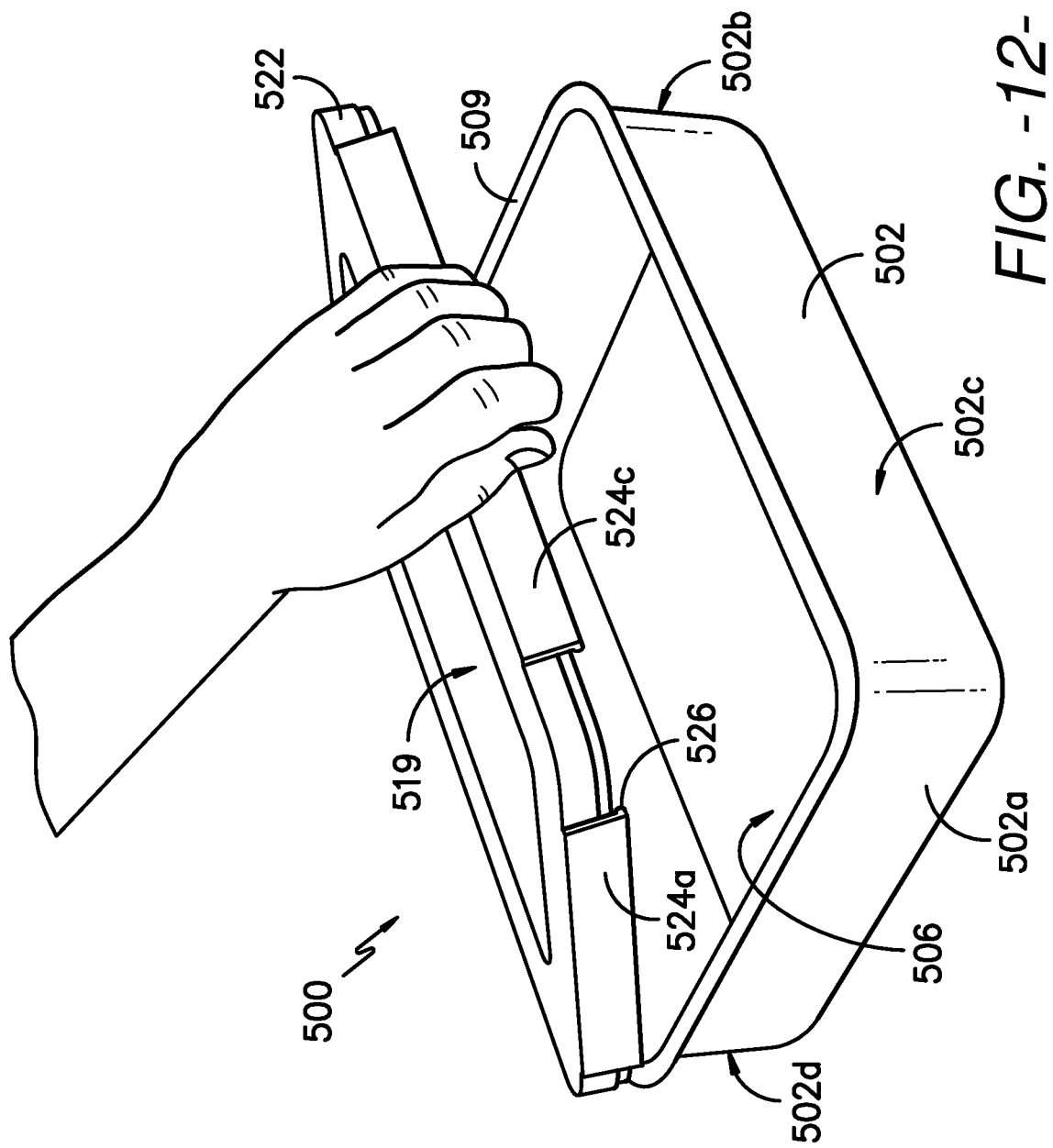
FIG. -12-

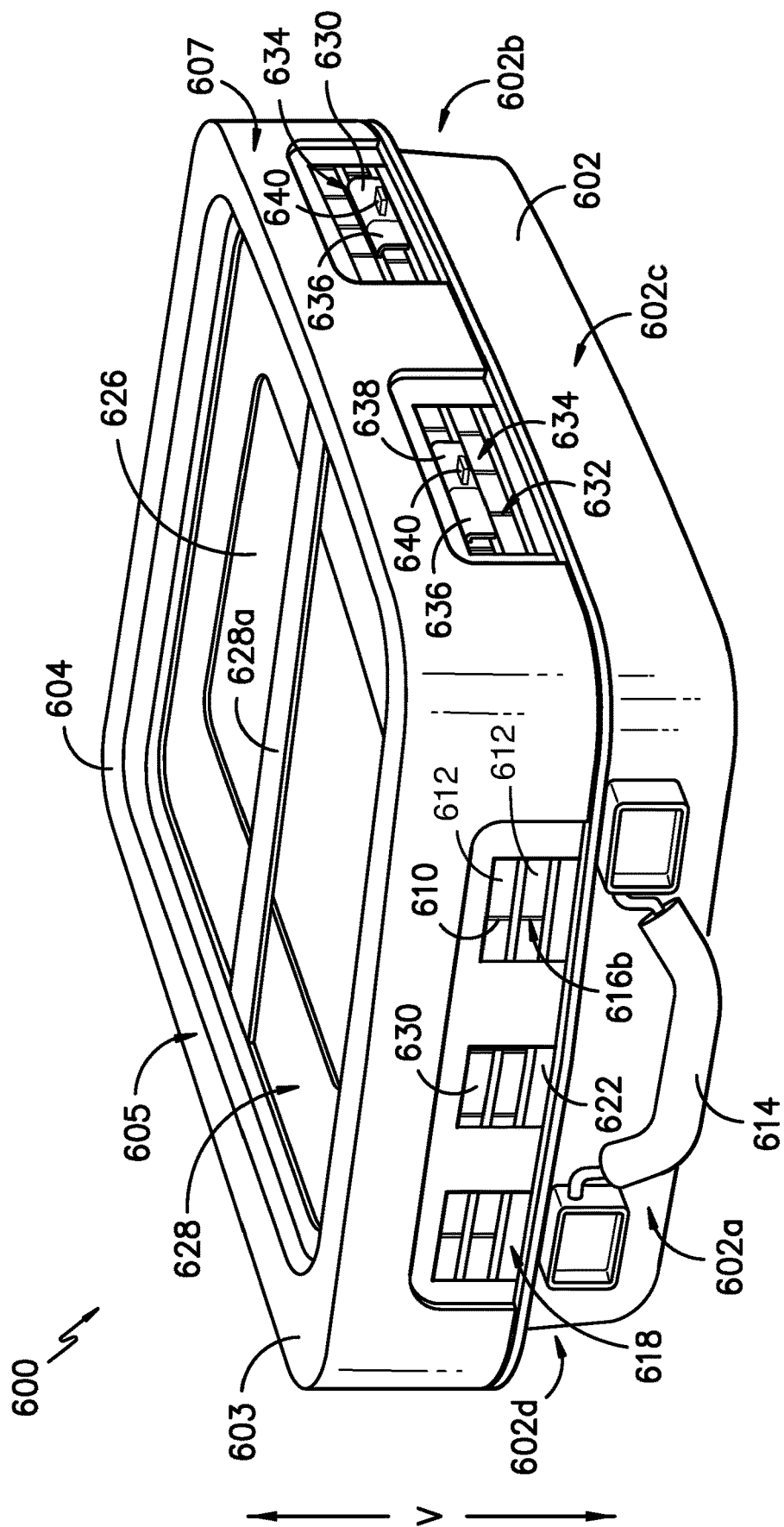
FIG. -13-

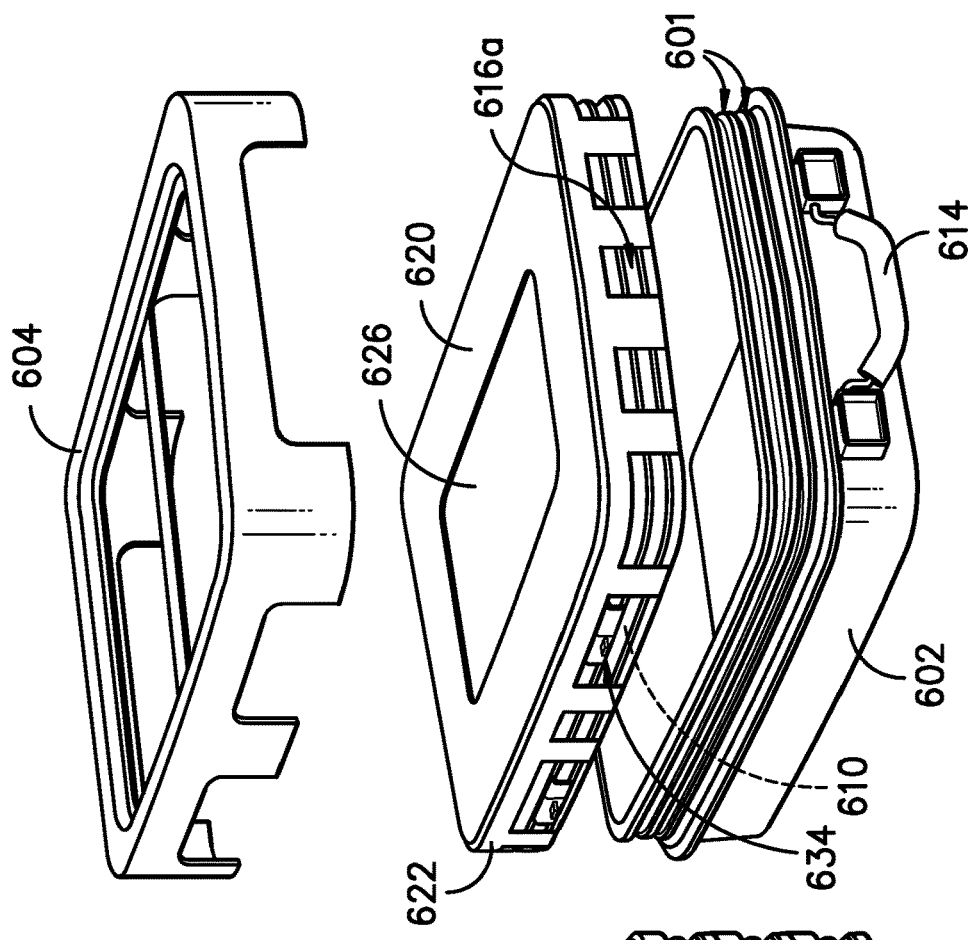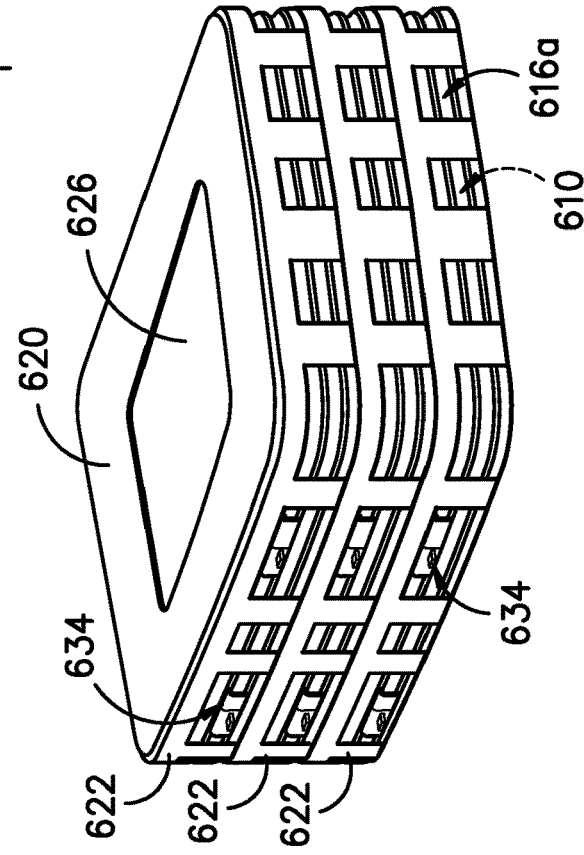
FIG. -14-

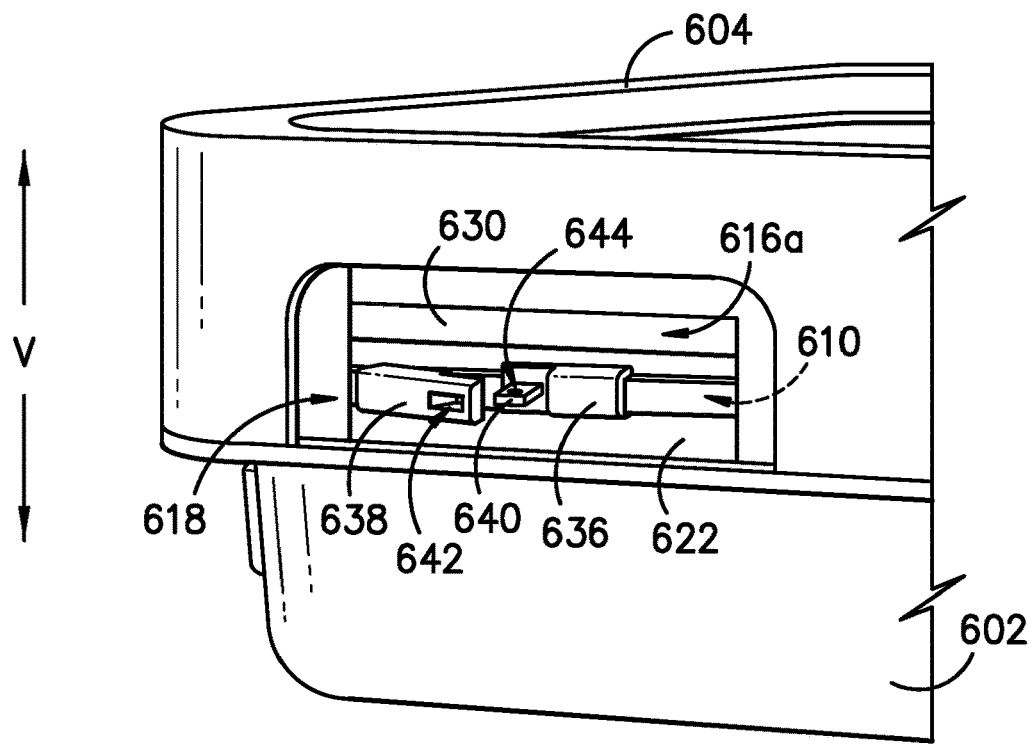
FIG. -15-
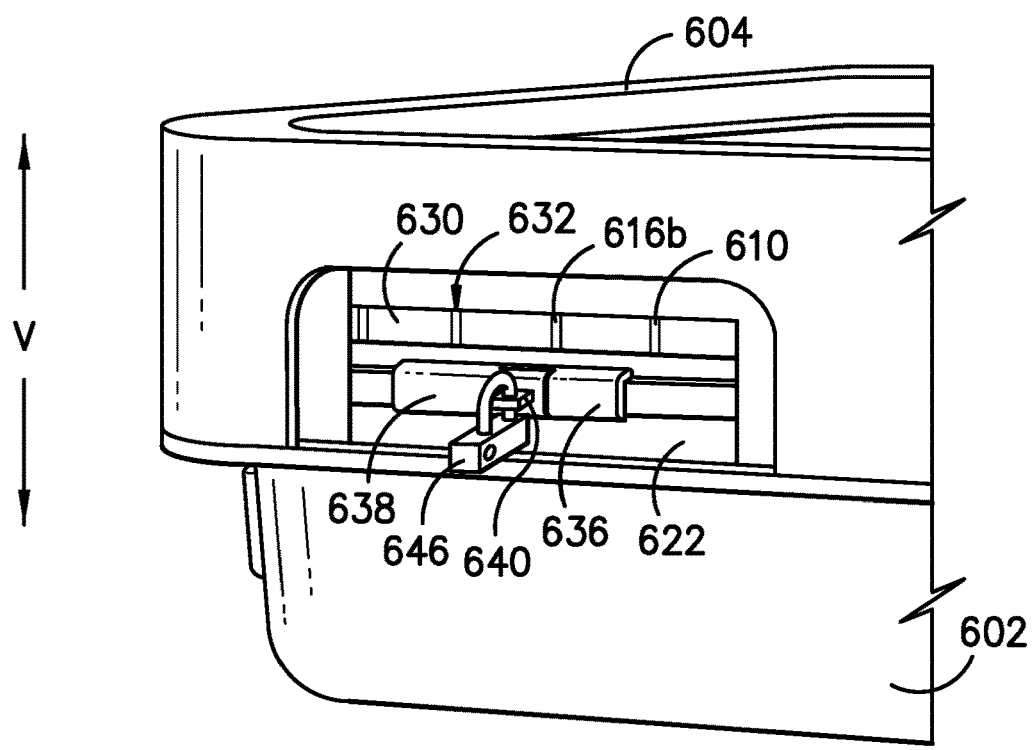
FIG. -16-

CLOSURE MECHANISMS AND SEAL INTEGRITY INDICATORS FOR STERILIZATION CONTAINERS

CROSS-REFERENCE TO RELATED APPLICATIONS

This application claims priority to U.S. Provisional Application Ser. No. 62/757,852, filed Nov. 9, 2018, the contents of which are incorporated herein by reference.

FIELD

The subject matter of the present disclosure relates generally to sterilization containers and, more particularly, to rigid sterilization containers with features for closing and sealing the sterilization container and for indicating that the sterilization container is properly sealed.

BACKGROUND

Personnel in a sterilization station, such as the Central Service Room (CSR) or the Sterile Processing Department (SPD) of hospitals, are commonly charged with the responsibility of packaging surgical supplies to ensure that the sterility of the packaged contents is maintained from sterilization to the point of reuse. Several activities are involved in the task of sterile supply delivery to the operating room and other units, such as a cardiac catheterization lab, emergency room, labor and delivery room, intensive care unit, pediatric care unit, specialized burn care units, and other surgical or medical units.

Many of the surgical instruments and supplies used in an operating room (OR), or other surgical or medical unit, are reusable. These supplies typically include such things as clamps, scalpel blade handles, retractors, forceps, scissors, surgeon's towels, basins, and the like. All of these supplies must be collected after each procedure, decontaminated, washed and dried before placing into a sterilization packaging system, and sterilized before they can be used again in another procedure. The sterilization packaging systems used must be of the size and shape to accommodate the items to be sterilized, must be compatible with and withstand the physical conditions of the cleaning, disinfection, and sterilization modality processes, and must be capable of maintaining the sterility of their contents post-sterilization.

Typical means of sterilizing surgical instruments, medical devices or accessories include, among others, steam sterilization (e.g., a dynamic-air-removal type such as a prevaccum cycle or steam-flush pressure-pulse (SFPP) cycle), exposure to ethylene oxide gas, and exposure to hydrogen peroxide plasma, as is done with the STERRAD® Sterilization System from Advanced Sterilization Products, Irvine, Calif. or as done with AMSCO V-PRO® Low Temperature Sterilization Systems using Vaporized Hydrogen Peroxide (VHP®) from STERIS. After the sterile barrier system and its contents have been sterilized, the sterilization sterile barrier system typically is stored until it is needed for a surgical or other medical procedure, or in some cases may be use immediately.

Common sterile barrier systems, also known as sterilization packaging systems, include sealable pouches, sterilization wraps, and rigid containers. Although each of these systems has some advantage compared to other systems, each of these typical packaging systems also has drawbacks. As an example, a rigid sterilization container will permit the entry of sterilizing vapor/gas or other medium to sterilize the contents of the container while denying the ingress of contaminants such as bacteria and other infection causing materials or their vehicles after sterilization. As such, rigid sterilization containers generally provide a consistent barrier against the ingress of contaminants. However, it is difficult to detect if the main seal of typical rigid sterilization containers is properly formed. That is, with the seal gasket integrated within the rigid sterilization container's lid, it is difficult to ascertain that the main seal has properly formed for maintaining the sterility of the container contents post sterilization. Further, it is difficult to detect if the seal gasket is damaged, which could hinder the gasket in the rigid sterilization container from creating an adequate seal against contamination reaching of the contents. Therefore, without opening the rigid sterilization container, one typically does not know if the main seal has maintained its closure or sterility has been maintained from when the rigid sterilization container left the sterilization station to when the contents of the rigid sterilization container are presented for use, e.g., in the OR, where aseptic presentation of the contents is desired. Moreover, most current rigid containers utilize a dual latching mechanism, i.e., a latch or lock on each end of the container, which does not adequately distribute the closure force along the four sides of the container.

Consequently, there is a need for a sterilization container that overcomes the shortcomings of known containers. In particular, an indicator for relatively quickly indicating to a user whether a sterilization container is or is not properly sealed, without requiring the user to open the container, would be advantageous. A sterilization container incorporating a visual seal indicator would be desirable. A sterilization container having improved means for closing the container, e.g., to ensure the container is properly sealed, also would be beneficial. For example, a closure mechanism that adequately and uniformly distributes a closing force along the gasket would be useful.

SUMMARY

The present invention provides sterilization containers with features for attaching a lid to a body of the container to seal an interior volume against an ingress of contaminants. The present disclosure further provides features for closing and sealing a sterilization container such that the closure force is distributed more uniformly along a sealing gasket of the container. The present disclosure also provides visual seal indicators for indicating whether a sterilization container is sealed against an ingress of contaminants. Additional aspects and advantages of the invention will be set forth in part in the following description, may be apparent from the description, or may be learned through practice of the invention.

In one aspect, the present subject matter is directed to a sterilization container that comprises a body and a lid that together define an interior, a closure mechanism for securing the lid to the body, and a gasket for sealing the interior against an ingress of contaminants. The body includes a first end, a second end opposite the first end, a first side extending between the first and second ends, and a second side opposite the first side and extending between the first and second ends. The body further includes an open top portion. The closure mechanism compresses the gasket between the lid and the body to seal the interior against the ingress of contaminants.

In another aspect, the present subject matter is directed to a sterilization container that comprises a body and a lid that together define an interior, a gasket for sealing the interior against an ingress of contaminants, and a seal indicator for indicating a seal state of the sterilization container. The seal indicator has a first indicator state that indicates an unsealed container state and a second indicator state that indicates a sealed container state. The seal indicator is in the first indicator state when the gasket is not compressed to seal the sterilization container against the ingress of contaminants, and the seal indicator is in the second indicator state when the gasket is compressed to seal the sterilization container against the ingress of contaminants.

In still another aspect, the present subject matter is directed to a sterilization container that comprises a body and a lid that together define an interior, a closure mechanism for securing the lid to the body, a combination gasket/filter, and a seal indicator for indicating a seal state of the sterilization container. The combination gasket/filter has a gasket for sealing the interior against an ingress of contaminants integrally formed with filter media for forming a barrier between an external environment and the interior. The seal indicator has a first indicator state that indicates an unsealed container state and a second indicator state that indicates a sealed container state. The closure mechanism compresses the combination gasket/filter between the lid and the body to seal the interior against the ingress of contaminants. The seal indicator is configured to display a first indicium in the first indicator state and is configured to display a second indicium in the second indicator state.

These and other features, aspects, and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which:

FIG. 1 provides a perspective view of a sterilization container in a closed state, where the sterilization container is sealed against an ingress of contaminants, according to an exemplary embodiment of the present subject matter.

FIG. 2 provides a perspective view of the sterilization container of FIG. 1 in an open state, where the sterilization container is not sealed against the ingress of contaminants.

FIG. 3 provides a perspective view of a sterilization container in a closed state, where the sterilization container is sealed against an ingress of contaminants, according to another exemplary embodiment of the present subject matter.

FIG. 4 provides a schematic cross-section view of a sterilization container in an open state, with a visual seal indicator indicating a corresponding first seal state of the sterilization container.

FIG. 5 provides the schematic cross-section view of FIG. 4, with the sterilization container in a closed state and the visual seal indicator indicating a corresponding second seal state of the sterilization container.

FIG. 6 provides a perspective view of a sterilization container in a closed state, where the sterilization container is sealed against an ingress of contaminants, according to another exemplary embodiment of the present subject matter.

FIG. 7 provides an exploded view of the sterilization container of FIG. 6.

FIG. 8 provides a cross-section view of a sealing assembly and a portion of a latch assembly of a sterilization container, according to an exemplary embodiment of the present subject matter.

FIG. 9 provides a perspective view of a sterilization container in a closed state, where the sterilization container is sealed against an ingress of contaminants, according to yet another exemplary embodiment of the present subject matter.

FIG. 10 provides an exploded view of the sterilization container of FIG. 9, as well as a perspective view of additional lid and combination gasket/filter assemblies that may be used with the sterilization container.

FIG. 11 provides a perspective view of a portion of the sterilization container of FIG. 9, illustrating a lid of the sterilization container in an unsecured state, in which the sterilization container is unsealed, and a secured state, in which the sterilization container is sealed.

FIG. 12 provides a perspective view of the sterilization container of FIG. 9 with the lid of the sterilization container being manipulated by a user.

FIG. 13 provides a perspective view of a sterilization container in a closed state, where the sterilization container is sealed against an ingress of contaminants, according to still another exemplary embodiment of the present subject matter.

FIG. 14 provides an exploded view of the sterilization container of FIG. 13, as well as a perspective view of additional combination gasket/filter assemblies that may be used with the sterilization container.

FIG. 15 provides a perspective side view of a portion of the sterilization container of FIG. 13, with a first end member of a gasket of the combination gasket/filter unsecured from a second end member of the gasket such that the gasket is in an untightened or non-stretched configuration.

FIG. 16 provides the perspective side view of FIG. 15, with the first end member secured with the second end member such that the gasket is in a tightened or stretched configuration to seal the sterilization container and with a tag, such as a tamper evidence tag, secured at the first and second end members.

DETAILED DESCRIPTION

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention covers such modifications and variations as come within the scope of the appended claims and their equivalents.

Described herein are a sterilization packaging system or container and components thereof suitable for use in a variety of procedures for containing, sterilizing, storing, and using sterilized items such as surgical devices, instruments, or supplies. While described in conjunction with its use in surgical room procedures located in hospitals or ambulatory surgical facilities, the present subject matter is intended for use wherever there is a need for containerized sterilized devices, instruments, or materials. Consequently, the following description should not be considered a limitation as to the scope of use of the present subject matter.

Generally, the present subject matter provides closure mechanisms for closing and/or sealing a container against an ingress of contaminants, as well as indicators for indicating the integrity of a seal. For example, described herein are various closure mechanisms for sterilization containers that apply a more uniform force to a sealing gasket of the container. A more uniform force along the gasket can help ensure the gasket establishes a proper seal between a lid and a base or body of the container, as well as retains the seal between the lid and body over time, e.g., before, during, and after a sterilization process, which includes delivery of a sterilization agent such as steam, ethylene oxide, hydrogen peroxide plasma, etc. to an interior of the container to sterilization the container's contents.

Further, described herein are seal indicators of sterilization containers that indicate whether the sterilization container is sufficiently sealed to prevent an ingress of contaminants into the sterilization container. If the sterilization container is sufficiently sealed, the seal indicator is in one state, and if the sterilization container is not sufficiently sealed, the seal indicator is in another state. Thus, the state of the sterilization container is communicated to a user through visible indicia of the seal indicator. That is, the seal indicator undergoes a visible change in state when the sterilization container transitions from not being sealed, e.g., when articles are being placed in the container for sterilization, to being sealed, e.g., when a lid of the container is properly secured to a body of the container, such that the user may be assured that the container is properly sealed to maintain sterility of the articles therein post-sterilization. Moreover, the seal indicator undergoes a visible change in state if the seal is broken after the lid is secured to the container, to signal to the user that the seal has been breached such that the articles in the container may no longer be sterile. However, the seal indicator does not undergo a state change when the container is subjected to a sterilization process or protocol, i.e., the state change associated with the closure or sealing of sealing of the container is unaffected by the sterilization modality. The present subject matter also provides methods for indicating a seal state of a sterilization container.

Turning now to FIGS. 1 through 3, additional embodiments of the present subject matter will be described. FIGS. 1 and 2 each provide a perspective view of a sterilization container 300 comprising a body 302 and a cover or lid 304, according to an exemplary embodiment of the present subject matter. FIG. 3 provides a perspective view of the container 300, having the body 302 and lid 304, according to another exemplary embodiment of the present subject matter. The body 302 and lid 304 together define an interior 306 of the sterilization container 300. One or more articles, e.g., clamps, scalpel blade handles, retractors, forceps, scissors, surgeon's towels, basins, and like surgical devices, instruments, or supplies, may be placed in the interior 306 of the container 300 for sterilization such that the article(s) may be reused in another procedure. It will be appreciated that the sterilization container 300 may generally have the form of a parallelepipedal box shape as shown in FIGS. 1-3, and the container 300 may have any appropriate size for containing the article(s) to be sterilized.

In FIGS. 1 and 3, the sterilization container 300 is closed and sealed against an ingress of contaminants. That is, the body 302 includes an open top portion 308, but when the lid 304 is secured to the body 302 as shown in FIGS. 1 and 3, the lid 304 covers the open top portion 308 of the body 302 and a gasket 310 (FIGS. 4, 5) is compressed between the lid 304 and body 302 to seal the container 300 against an ingress of contaminants, as described in greater detail herein. In FIG. 2, the sterilization container 300 is open and, thus, is unsealed or not sealed against the ingress of contaminants. More specifically, the lid 304 is separated from the body 302 to expose the interior 306 of the container 300.

As shown in FIGS. 1 and 2, the lid 304 is retained on the body 302 by one or more latch assemblies 312, and in FIG. 3, the lid 304 is retained on the body 302 by one or more latch assemblies 350. The latch assemblies 312, 350 form a closure mechanism for securing the lid 304 to the body 302 and sealing the container interior 306 and are described in greater detail herein. Further, the container 300 includes one or more handles 314 for lifting, carrying, or otherwise handling the container 300. For example, a first handle 314 may be attached to a first end 302a of the body 302, and a second handle 314 may be attached to a second end 302b of the body 302, where the second end 302b is opposite the first end 302a. In other embodiments, a first handle 314 may be attached to a first side 302c of the body 302, and a second handle 314 may be attached to a second side 302d of the body 302, where the second side 302d is opposite the first side 302c and the first and second sides 302c, 302d extend between the first and second ends 302a, 302b. Other configurations and/or placements of one or more handles 314 may be used as well.

As further depicted in FIGS. 1-3, a visual indicator 316 provides a visual indication of a seal state of the sterilization container 300. For instance, the visual indicator 316 indicates to a user of the container 300 whether the container 300 is in a first, unsealed state, where the container 300 is not sealed against an ingress of contaminants (i.e., contaminants could enter the container 300), or a second, sealed state, where the container 300 is sealed against the ingress of contaminants (i.e., contaminants cannot enter the container 300). That is, the visual indicator 316 is a binary indicator of the integrity of the seal between the body 302 and lid 304 of the container 300, e.g., the indicator 316 indicates when the seal is established and when the seal is broken or otherwise comprised. More particularly, the seal indicator 316 has a first indicator state that indicates the unsealed container state and a second indicator state that indicates the sealed container state. The seal indicator 316 is visible to a user of the container 300 from the container exterior to signal to the user whether the container 300 is sealed or unsealed. A change in state, i.e., from the first indicator state to the second indicator state or from the second indicator state to the first indicator state, may be achieved by a change in color, shape, size, position, etc. of the seal indicator 316 to signal the container 300 has transitioned from its unsealed state to its sealed state or from its sealed state to its unsealed state. The change in state by the visible seal indicator 316 relatively quickly communicates to the user the seal state of the container 300, without requiring the user to open the container 300. Further, the seal indicator 316 is unaffected by the sterilization modality to which the container 300 is subjected to sterilize the articles within the container 300. The visual indicator 316 is described in greater detail herein.

As previously described, the seal between the container body 302 and lid 304 is established by the gasket 310. The gasket 310 extends between the body 302 and lid 304; for example, the gasket 310 extends about a perimeter of the open top portion 308 of the body 302 and an interface portion of the lid 304. Securing the lid 304 to the body 302 compresses the gasket 310 between the body 302 and lid 304 to seal the interior 306. When the gasket 310 is not compressed, or not fully compressed, such that the interior 306 is not sealed against the ingress of contaminants, the container 300 is in its first, unsealed state and the seal indicator 316 is in its first indicator state. Similarly, when the gasket 310 is fully compressed, such that the interior 306 is sealed against the ingress of contaminants, the container 300 is in its second, sealed state and the seal indicator 316 is in its second indicator state.

As described in greater detail herein, in some embodiments of seal indicators, such as seal indicator 316, the seal indicator is configured to display a first indicium in the first indicator state and is configured to display a second indicium in the second indicator state. The first indicium may be a first color or hue and the second indicium may be a second color or hue, and the first and second colors or hues may be selected such that there is a high contrast between the colors/hues and/or between the colors/hues and the sterilization container, and/or the colors/hues may be selected to reinforce the signal communicated by the color or hue. For example, in an exemplary embodiment, the first color is red to indicate the container 300 is unsealed (i.e., contaminants could enter the container 300 and reach any articles in the interior 306), and the second color is green to indicate the container 300 is sealed (i.e., contaminants cannot enter the container 300 and any articles in the container 300 would remain sterile after sterilization). Thus, the seal indicator 316 is configured to display the first color when the container 300 is unsealed and the second color when the container 300 is sealed, such that the seal indicator 316 indicates a change in the seal state of the container 300 through a change in color.

Further, as previously stated, rather than a dual colored indicator, the seal indicator 316 may comprise other features for indicating the seal state of the container 300. As an example, the first indicium may be a first visual pattern and the second indicium may be a second visual pattern, such that the seal indicator 316 displays the first pattern when the container 300 is in the first, unsealed state and displays the second pattern when the container 300 is in the second, sealed state. Other visual indicia, e.g., images, color differences, words, etc., and other types of indicators, such as auditory or other non-visual indicators, may be used as well.

Keeping with FIGS. 1 and 2, different configurations of the lid 304 are illustrated that may be used in the exemplary embodiment of container 300. As shown in FIG. 1, in some embodiments the lid 304 defines one or more vents 318 in a top surface 305 of the lid 304. In other embodiments of the lid 304, the lid 304 does not define vents 318 in the top surface 305, as shown in FIG. 2, but the vent(s) 318 are defined elsewhere in the container 300, e.g., in one or more side surfaces 307 of the lid 304 that are generally orthogonal to the top surface 305, in the body 302, or in both the lid 304 and the body 302. The vent(s) 318 permit fluids, such as air, steam, and chemical sterilization agents and/or other sterilants, to pass through the lid 304 and into the interior 306 of the sterilization container 300, e.g., to sterilize the contents of the container 300, as well as to pass from the interior 306 to an exterior environment, e.g., to help the contents of the container 300 dry after a sterilization process.

A filter (not shown) is positioned within the sterilization container 300 adjacent the vent(s) 318 to prevent contaminants from entering the interior 306. For example, the filter may be a sheet of material that extends over the open top portion 308 of the body 302 such that the filter is positioned between the lid 304 and the container interior 306. However, the filter need not be configured as a sheet but may have any suitable configuration or construction. Further, the filter can be made from a number of materials and, generally, may be made of a material from one of two main classes, reusables and disposables. Reusables are materials that, as the name suggests, can be reused, typically by washing or some other form of cleaning. Disposables, on the other hand, usually are one-use items that are discarded or recycled after their initial use. Generally, cloth, linen, or other woven materials fall into the reusable category while disposables normally include nonwoven materials made from either or both natural and synthetic fibers such as paper, fibrous polymeric nonwovens, and films, which are capable of passing sterilants and retarding transmission of bacteria and other contaminants.

Nonwoven sterilization materials present several advantages due to their barrier properties, economics, and consistent quality. The nonwoven materials can be made from a variety of processes including, but not limited to, air laying processes, wet laid processes, hydroentangling processes, spunbonding, meltblowing, staple fiber carding and bonding, and solution spinning. The fibers themselves can be made from a variety of both natural and synthetic materials including, but not limited to, cellulose, rayon, nylon, polyesters, polyolefins, and many other materials. The fibers may be relatively short, staple length fibers, typically less than three inches, or longer and substantially more continuous fibers such as are produced by spunbonding and meltblowing processes. Whatever materials are chosen, the resultant filter material must be compatible with the particular sterilization technique being used and must also provide both strength and barrier properties to maintain the sterile nature of the contents of the sterilization container 300 until use.

In some embodiments, the lid 304 may define a window through which the filter is visible to a user of the container 300, and the filter may also define a window, formed from a transparent breathable film or the like that still provides a barrier against contaminants, such that the user can see through the filter and into the interior 306 of the container 300. Such windows through the lid and filter allow the user to, e.g., verify contents of the container 300, reducing the need to open containers to find specific instrument sets, as well as view any internal indicators, if provided, which may be indicators of seal integrity or whether the container 300 has undergone a sterilization process. However, in other embodiments, the filter may be made from a translucent or opaque material, such as, e.g., an SMS material, polytetrafluoroethylene (PTFE), paper, or the like. For example, polyolefin-based fibers and their resultant nonwovens are particularly well-suited for the production of a flexible filter, and a polypropylene spunbonded nonwoven can be used to impart strength characteristics to the filter. In some embodiments, the filter may be made from laminates such as a laminate of spunbonded and meltblown or spunbonded, meltblown, spunbonded to impart both strength and barrier properties to the filter. A spunbonded-meltblown-spunbonded (SMS) material is made from three separate layers that are laminated to one another. The method of making these layers is known and described in U.S. Pat. No. 4,041,203 to Brock, et al., which is incorporated herein in its entirety by reference. The material of Brock, et al. is a three layer laminate of spunbonded-meltblown-spunbonded layers. The two outer layers of SMS are a spunbonded material made from extruded polyolefin fibers, or filaments, laid down in a random pattern and then bonded to one another. The inner layer is a meltblown layer also made from extruded polyolefin fibers generally of a smaller diameter than the fibers in the spunbonded layers. As a result, the meltblown layer provides increased barrier properties due to its fine fiber structure, which permits the sterilizing agent to pass through the fabric while preventing passage of bacteria and other contaminants. Conversely, the two outer spunbonded layers provide a greater portion of the strength factor in the overall laminate. The laminate may be prepared using an intermittent bond pattern that is preferably employed with the pattern being substantially regularly repeating over the surface of the laminate. The pattern is selected such that the bonds may occupy about 5% to about 50% of the surface area of the laminate. Desirably, the bonds may occupy about 10% to about 30% of the surface area of the laminate. In an exemplary embodiment, the filter is made from an SMS material, but the filter also may be made from other suitable materials.

With respect to FIG. 3, although shown without vents 318 in the lid 304, it will be appreciated that the sterilization container 300 is vented in some fashion to allow fluids, such as air and sterilants, to enter and exit the container 300. As described with respect to FIGS. 1 and 2, in some embodiments, the vents 318 are defined in the top surface 305 of the lid 304, but in other embodiments, the vents 318 are defined in one or more side surfaces 307 of the lid 304 that are generally orthogonal to the top surface 305. In other embodiments, the vents 318 may be defined in the body 302, or in both the lid 304 and the body 302. As previously described, a filter is disposed between the vent openings 318 and the container interior 306 to prevent contaminants from entering the interior 306.

Referring still to FIGS. 1-3, the lid 304 has top surface 305 that faces away from the body 302. Further, the lid 304 includes a first end 304a opposite a second end 304b and a first side 304c opposite a second side 304d. The first and second sides 304c, 304d extend between the first and second ends 304a, 304b. Once the lid 304 is secured to the body 302 as described in greater detail below, the gasket 310 is compressed between the body 302 and lid 304, preventing contaminants from entering the container interior 306 defined by the body 302 and lid 304.

Referring particularly to FIGS. 1 and 2, the container 300 includes a latch assembly 312 for securing the lid 304 to the body 302 and for compressing the gasket 310 between the lid 304 and body 302 to seal the interior 320. The latch assembly 312 is symmetrical about a longitudinal midline $L_M$ of the lid 304 such that the latch assembly 312, as well as the remainder of the container 300, is the same on a first half that includes the lid first end 304a and body first end 302a as on a second half that includes the lid second end 304b and body second end 302b. Thus, it will be understood that, although not shown completely in the figures, the lid second end 304b and body second end 302b include the same or identical features as shown on the lid first end 304a and body first end 302a, and the lid second side 304d and body second side 302d include the same or identical features as shown on the lid first side 304c and body first side 302c.

In the exemplary embodiment shown in FIGS. 1 and 2, the latch assembly 312 includes a first arm 322 attached to the lid 304 and pivotable with respect to the lid 304, a second arm 324 attached to the lid 304 and pivotable with respect to the lid 304, a pair of first hooks 326 extending from the first arm 322 to the body 302, and a pair of second hooks 328 extending from the second arm 324 to the body 302. Additionally, the latch assembly 312 includes a pair of end latches 330; a first end latch 330 is attached to the first arm 322 and a second end latch 330 is attached to the second arm 324. The first arm 322 extends about a first portion 305a of the top surface 305 of the lid 304, and the second arm 324 extends about a second portion 305b of the top surface 305 of the lid 304.

To secure the lid 304 with respect to the body 302, the hooks 326, 328 engage the sides 302c, 302d of the body 302 and the end latches 330 engage the ends 302a, 302b of the body 302. More particularly, one first hook 326 releasably attaches to a side catch 334 on the first side 302c of the body 302 and the other first hook 326 releasably attaches to a side catch 334 on the second side 302d of the body 302 to compress the first arm 322 against the lid 304. To compress the second arm 324 against the lid 304, one second hook 328 releasably attaches to a first side catch 336 on the first side 302c of the body 302 and the other second hook 328 releasably attaches to a second side catch 336 on the second side 302d of the body 302. Further, the first arm end latch 330 extends from the first arm 322 to the body 302 and engages an end catch 338 on the first end 302a of the body 302. Similarly, the second arm end latch 330 extends from the second arm 324 to the body 302 and engages a second end catch 338 on the second end 302b of the body 302. As best illustrated in FIG. 2, each end catch 338 may be disposed on a portion of the respective body end 302a, 302b that is recessed with respect to the remainder of the end 302a, 302b.

It will be appreciated from FIGS. 1 and 2 that each of the end latches 330 includes at least one element that is pivotable or rotatable with respect to the respective first arm 322 or second arm 324 to engage and to disengage from the body 302. For example, a support 340 may be attached to each arm 322, 324, and a pin 342 may extend through each end latch 330 to pin the latch to its respective support 340. As such, the respective end latch 330 is secured to its support 340 but can pivot or rotate about its pin 342. By grasping the end latch 330 and pivoting or rotating the end latch 330 with respect to its arm 322, 324, a user can disengage the end latch 330 from its respective end catch 338 or engage the end latch 330 with its respective end catch 338.

Additionally, in the depicted exemplary embodiment, each of the first arm 322 and the second arm 324 are formed from a generally cylindrical material such that each arm 322, 324 has a generally circular or round cross-section. For example, each arm 322, 324 may be formed from a relatively thick metallic wire that is manipulated into the desired outline for each arm 322, 324, e.g., by bending. More particularly, the first arm 322 comprises a first segment 322a, a second segment 322b, and a third segment 322c. The first, second, and third segments 322a, 322b, 322c of the first arm 322 are arranged such that the first portion 305a of the lid top surface 305 includes the lid first end 304a, a portion of the lid first side 304c, and a portion of the lid second side 304d. An end 344 of each of the first and third segments 322a, 322c of the first arm 322 is secured to the lid 304 near the longitudinal midline $L_M$ of the lid 304. The first arm 322 pivots about the ends 344. Similarly, the second arm 324 comprises a first segment 324a, a second segment 324b, and a third segment 324c such that the second arm 324 is a mirror image of the first arm 322. The first, second, and third segments 324a, 324b, 324c of the second arm 324 are arranged such that the second portion 305b of the lid top surface 305 includes the lid second end 304b, a portion of the lid first side 304c, and a portion of the lid second side 304d. An end 346 of each of the first and third segments 324a, 324c of the second arm 324 is secured to the lid 304 near the longitudinal midline $L_M$ of the lid 304. The second arm 324 pivots about the ends 346.

Moreover, the lid 304 defines a groove 348 in its top surface 305 for receipt of each of the first arm 322 and the second arm 324. The groove 348 is defined inward of each of the first and second ends 304a, 304b and first and second sides 304c, 304d of the lid 304 such that the groove 348 is offset from each of the first and second ends 304a, 304b and first and second sides 304c, 304d of the lid 304. Further, the groove 348 has a shape complementary to the shape of the first arm 322 and the second arm 324 such that both the first arm 322 and second arm 324 are recessed within the groove 348 when the first and second arms 322, 324 are received in the groove 348.

Accordingly, the exemplary embodiment of the sterilization container 300 shown in FIGS. 1 and 2 features a closure mechanism that may be referred to as a picnic basket-style closure mechanism. To open the container 300, each arm 322, 324 on top of the lid 304 pivots upward toward a plane extending through the longitudinal midline $L_M$ of the lid 304, which is the longitudinal center of the container 300. To close the container 300, the arms 322, 324 pivot downward until they are received in the groove 348 defined in the lid 304. End latches 330 and side hooks 326, 328 extend from the arms 322, 324 and attach to the container body 302 to secure the lid 304 to the body 302 and to compress the gasket 310 to seal the interface between the lid 304 and body 302 such that contaminants cannot interior the container interior 320.

Turning now to FIG. 3, an alternative exemplary embodiment of the picnic basket-style closure mechanism for exemplary sterilization container 300 will be described. Similar to the embodiment shown in FIGS. 1 and 2, the embodiment shown in FIG. 3 has a latch assembly 350 for securing the lid 304 to the body 302 and compressing the gasket 310 between the lid 304 and body 302. The latch assembly 350 includes a pair of arms 352, 354 that each extend around a portion of the top surface 305 of the lid 304 to secure the lid 304 to the body 302. However, unlike the embodiment of FIGS. 1 and 2, in which the arms 322, 324 are offset from an outer edge 303 of the lid 304, the arms 352, 354 of the embodiment of FIG. 3 extend around the edge 303 of the lid 304. The first arm 352 extends around the first end 304a and a portion of each of the first and second sides 304c, 304d of the lid 304, and the second arm 354 extends around the second end 304b and a portion of each of the first and second sides 304c, 304d of the lid 304. Each of the first arm 352 and second arm 354 is hinged near the lid longitudinal midline $L_M$; that is, each arm 352, 354 is pivotably attached to the lid 304 near the longitudinal midline $L_M$ such that the arms 352, 354 can pivot toward and away from the lid 304. The arms 352, 354 pivot upward or away from the lid 304 to unsecure the lid 304 from the body 302 the sterilization container 300, and the arms 352, 354 pivot downward or toward the lid 304 to secure the lid 304 with respect to the body 302 and to seal the container interior 306 against the ingress of contaminants.

Similar to the embodiment illustrated in FIGS. 1 and 2, the latch assembly 350 of the embodiment illustrated in FIG. 3 further includes a pair of first hooks 356 extending from the first arm 352 and a pair of second hooks 358 extending from the second arm 354. Each of the first hooks 356 and second hooks 358 extend downward from the lid 304 toward the body 302. Additionally, the latch assembly 350 includes a pair of end latches 360; the first arm 352 includes a first end latch 360, and the second arm 354 includes a second end latch 360. Like the hooks 356, 358, the end latches 360 extend downward from their respective arms 352, 354 toward the body 302.

To secure the lid 304 with respect to the body 302, each of the first arm 352 and second arm 354 pivots down into place along the outer edge 303 of the lid 304. When the arms 352, 354 are in position against the lid 304, the hooks 356, 358 engage the sides 302c, 302d of the body 302 and the end latches 360 engage the ends 302a, 302b of the body 302. More particularly, one first hook 356 releasably attaches to a first side catch 364 on the first side 302c of the body 302 and the other first hook 356 releasably attaches to another first side catch 36r on the second side 302d of the body 302 to compress the first arm 352 against the lid 304. To compress the second arm 354 against the lid 304, one second hook 358 releasably attaches to a second side catch 366 on the first side 302c of the body 302 and the other second hook 358 releasably attaches to another second side catch 366 on the second side 302d of the body 302. Further, the first end latch 360 engages a first end catch 368 on the first end 302a of the body 302. Similarly, the second end latch 360 extends from the second arm 354 to the body 302 and engages a second end catch 368 on the second end 302b of the body 302.

It will be appreciated from FIG. 3 that each of the end latches 360 includes at least one element that is pivotable or rotatable with respect to the respective first arm 352 or second arm 354 to engage and to disengage from the body 302. For example, a support 370 may be attached to each arm 352, 354, and a pin 372 may extend through each end latch 360 to pin the latch to its respective support 370. As such, the respective end latch 360 is secured to its support 370 but can pivot or rotate about its pin 372. By grasping the end latch 360 and pivoting or rotating the end latch 360 with respect to its arm 352, 354, a user can disengage the respective end latch 360 from its respective end catch 368 or engage the end latch 360 with its end catch 368.

As shown in the embodiment of FIG. 3, the lid 304 defines a recess 378 around the outer edge 303 of the lid 304. The recess 378 has a shape complementary to both the first arm 352 and the second arm 354 for receipt of the arms 352, 354. Each of the first arm 352 and the second arm 354 pivots into the recess 378 and the end latches 360 and hooks 356, 358 engage their respective catches to compress the lid 304 between the first and second arms 352, 354 and the body 302.

Further, similar to the embodiment of FIGS. 1 and 2, in the embodiment of FIG. 3, the first arm 352 comprises a first segment 352a, a second segment 352b, and a third segment 352c. An end 374 of each of the first and third segments 352a, 352c of the first arm 352 is secured to the lid 304 near a longitudinal midline $L_M$ of the lid 304. The first arm 352 pivots about the ends 374. Moreover, the second arm 354 comprises a first segment 354a, a second segment 354b, and a third segment 354c such that the second arm 354 is a mirror image of the first arm 352. An end 376 of each of the first and third segments 354a, 354c of the second arm 354 is secured to the lid 304 near the longitudinal midline $L_M$ of the lid 304, and the second arm 354 pivots about the ends 376.

As shown in the embodiments of FIGS. 1-3, the end latches 330, 360 extend from the respective first arm 322, 352 or second arm 324, 354, which is attached the lid 304, to an end catch 338, 368 on the body 302. However, in alternative embodiments, rather than being attached to the first arms 322, 352 and second arms 324, 254 of the lid 304, the end latches 330, 360 could be attached to the body 302, e.g., using pins 342, 372 such that the latches 330, 360 pivot with respect to the body 302. In such alternative embodiments, the first end latches 330, 360 would pivot upward from the body 302 toward the lid 304 and catch on the first arm 322, 352, either in a first end catch 338 defined in the first arm 322, 352 or by fitting partially around or over the first arm 322, 352. Similarly, the second end latches 330, 360 would pivot upward from the body 302 toward the lid 304 and catch on the second arm 324, 354, either in an end catch 338, 368 defined in the second arm 324, 354 or by fitting partially around or over the second arm 324, 354. Of course, in alternative embodiments, the first hooks 326, 356 and second hooks 328, 358 also could be reversed such that they extend from the body 302 to the lid 304, i.e., to the first arm 322, 352 and second arm 324, 354 of the lid 304. Other alternative configurations may be utilized as well.

It will be appreciated that the picnic basket-style closures described with respect to FIGS. 1-3 provide a more even pressure distribution along the gasket 310 than typical sterilization containers, which generally include one latch on each end of the container. That is, the multiple latches 330, 360 and hooks 326, 328, 356, 358 spaced about the entire perimeter of the sterilization container 300 provide several more locations than typical containers where force is applied to keep the lid 304 secured to the body 302. Further, the arms 322, 324, 352, 354 help distribute the pressure or force applied by the hooks 326, 328, 356, 358 and latches 330, 360 to more evenly compress the gasket 310 between the lid 304 and body 302. A more evenly distributed force or pressure on the gasket 310 provides a better seal, helping to prevent the ingress of contaminants to the container interior 306, e.g., by resisting loss of the seal over time. For instance, with additional latches and hooks and arms that distribute the sealing pressure as described with respect to the exemplary embodiments, the seal can be maintained even if one or more latches or hooks loosen (or apply less force) over time. Of course, other advantages and benefits also may be realized from the closure mechanisms described with respect to FIGS. 1-3.

Referring still to FIGS. 1-3, as well as to FIGS. 4 and 5, in the illustrated exemplary embodiments, the sterilization container 300 includes a gasket channel 380 that extends around the perimeter of the lid 304. The gasket channel 380 includes an inner segment 382, a lateral segment 384, and an outer segment 386, and a channel or groove is defined between the inner segment 382 and outer segment 386, with the lateral segment 384 forming the vertical boundary of the channel or groove. The gasket 310 extends within the channel or groove of the gasket channel 380. In alternative embodiments, the gasket channel 380, with the gasket 310 positioned therein, could extend around the perimeter of the open top portion 308 of the body 302 rather than around the lid 304. In any event, the gasket channel 380 and gasket 310 are arranged such that the gasket 310 lines the interface between the body 302 and lid 304 of the container 300 to seal the container interior 306 against the ingress of contaminants when the lid 304 is secured to the body 302. For example, either the rim of the body 302 is received within the gasket channel 380 included with the lid 304 or the rim of the lid 304 is received within the gasket channel 380 included with the body 302 to compress the gasket 310 and seal the container 300 when the latches 330, 360 and hooks 326, 328, 356, 358 secure the lid 304 to the body 302 as described with respect to FIGS. 1-3.

In an exemplary embodiment, the gasket channel 380 is transparent such that the gasket 310 within the gasket channel 380 is visible to a user of the container 300. The transparent gasket channel 380 may be formed from a high temperature resistant material, such as Radel® polyphenylsulfone (PPSU). As described herein with respect to various sterilization container embodiments, the gasket 310 may be the seal indicator 316 having a first indicator state and a second indicator state, i.e., the gasket 310 is configured to display a first indicium 310a when the container 300 is in a first, unsealed state and a second indicium 310b when the container 300 is in a second, sealed state. Because the gasket channel 380 is transparent, it provides a window for viewing the gasket 310 and the first and second indicia 310a, 310b thus are visible to the user through the gasket channel 380. In exemplary embodiments, the first indicium 310a is a first color or hue and the second indicium 310b is a second color or hue. The first and second colors/hues may be contrasting or complementary colors, e.g., the first and second colors/hues may be selected such that there is a high contrast between the colors/hues (e.g., to enable clear differentiation between the first indicium 310a and second indicium 310b) and/or between the colors/hues and the sterilization container 300, and/or the colors/hues may be selected to reinforce the signal communicated by the color or hue. For instance, in an exemplary embodiment, the first color is red to indicate the container 300 is unsealed (i.e., contaminants could enter the container 300 and reach any articles in the interior 306), and the second color is green to indicate the container 300 is sealed (i.e., contaminants cannot enter the container 300 and any articles in the container 300 would remain sterile after sterilization). Thus, the seal indicator provided by the gasket 310 is configured to display the first color when the container 300 is unsealed and the second color when the container 300 is sealed, such that the gasket 310 indicates a change in the seal state of the container 300 through a change in color. As described in more detail herein, in other embodiments, the gasket 310 may utilize other features for indicating the seal state of the container 300 or the integrity of the gasket 310, e.g., other binary visual indicia such as patterns, images, and/or words; other visual state changes such as changes in position, shape, and/or size; and/or auditory or other non-visual indicators.

FIGS. 4 and 5 depict the seal indicator features of the gasket 310 in greater detail, according to an exemplary embodiment of the present subject matter. As shown in FIGS. 4 and 5, the gasket comprises, along the vertical direction V, a top portion 388, a middle portion 390, and a bottom portion 392. At least one of the top portion 388 and the bottom portion 392 include the second indicium 310b, and the middle portion 390 includes the first indicium 310a. Accordingly, the middle portion 390 and the first indicium 310a are visible to the user in the unsealed state, i.e., when the gasket 310 is not compressed to seal the container 300. The middle portion 390 is compressible such that the top portion 388 meets the bottom portion 392 when the gasket 310 is compressed in the sealed state and only the second indicium 310b is visible to the user, thereby indicating the container 300 is sealed. More particularly, the gasket 310 is notched or has a generally hourglass cross-sectional shape such that the gasket 310 is thinner in the middle portion 390 than in the top portion 388 or bottom portion 392. Further, the gasket 310 may be formed from a compressible or deformable material. Accordingly, when the lid 304 is positioned on the body 302 and a generally downward force is applied to the lid 304, the top portion 388 of the gasket 310 is forced toward the bottom portion 392 of the gasket 310, with the middle portion 390 compressed between the top and bottom portions 388, 392. As illustrated in FIGS. 4 and 5, at least the top portion 388 includes a flange 394, which extends downward toward the bottom portion 392. When the lid 304 is not secured to the body 302 as shown in FIG. 4, the flange 394 at least does not extend the entire height of the middle portion 390 such that the middle portion 390 and the first indicium 310a are visible to the user through the outer segment 386 of the gasket channel 380. However, referring to FIG. 5, when the lid 304 is secured to the body 302, e.g., by attaching the hooks 326 to the side catches 334 to latch the first arm 322 in place within the groove 348, the flange 394 extends between the compressed middle portion 390 and the outer segment 386 over the entire height of the compressed middle portion 390 such that only the second indicium 310b, which is carried or embodied by the top and bottom portions 388, 392, is visible to the user through the outer segment 386 of the gasket channel 380. Thus, the gasket 310, when functioning as a seal as well as the seal indicator 316, is collapsible when compressed to transition from displaying both the first indicium 310a and the second indicium 310b (when the gasket 310 is uncompressed and the container 300 is unsealed) to displaying only the second indicium 310b (when the gasket 310 is compressed and the container 300 is sealed).

Of course, in some embodiments, the gasket channel 380 may include features, such as a mask or other opaque material, such that only the first indicium 310a is visible when the gasket 310 is not compressed. Further, in some embodiments, only the outer segment 386 of the gasket channel 380 may be fully or partially transparent, i.e., the inner and lateral segments 382, 384 need not be transparent because a user cannot look through the inner and lateral segments 382, 384 to view the gasket 310. Moreover, the gasket channel 380 or the outer segment 386 may be transparent along the entire perimeter of the container 300 such that the gasket 310 is visible along the entire container perimeter and, thus, is a continuous indicator along the perimeter. However, in other embodiments, the gasket channel 380 or the outer segment 386 may be transparent only in certain locations along the perimeter, e.g., in one location on each end and side of the container 300, such that the gasket 310, and thereby the indicator 316, is visible only at those certain locations. In still other embodiments, the seal indicator 316 may be separate from the gasket 310 but may be configured similarly to the gasket seal indicator described above.

Referring still to FIGS. 4 and 5, in other embodiments, the seal state of the container 300 may be indicated by state change of the seal indicator 316 that relies on an interaction between the gasket 310 and the gasket channel 380. As previously described, at least the outer segment 386 of the gasket channel 380 is formed from a transparent material such that the gasket 310 is visible through the outer segment 386. The flange 394 of the top portion 388 of the gasket 310 may be configured to contact an inner surface 396 of the outer segment 386 when the lid 304 is secured to the body 302 and the gasket 310 is sufficiently compressed to seal the interior 306. When the flange 394 contacts the inner surface 396, there is a visible change at the gasket channel 380. For example, the gasket 310 may be yellow and the transparent outer segment 386 may be tinted blue such that when the yellow flange 394 contacts the transparent blue outer segment 386, a green stripe (or other marking) is visible at the gasket channel 380. Of course, other color combinations may be used as well. Further, the gasket 310 may be spaced from the outer segment 386 such that it is not clearly visible when uncompressed, but when the flange 394 contacts the outer segment inner surface 396, a stripe (or other marking) is visible at the gasket channel 380. Other visual state changes, such as changes in pattern, shape, color, and size as described herein, may be used as well. Accordingly, in such embodiments, the first indicator state is when the flange 394 is not in contact with the outer segment inner surface 396, which is signaled by any appropriate visual state of the seal indicator 316 as described herein, and the second indicator state is when the flange is in contact with the outer segment inner surface 396, which is signaled by any appropriate visual state of the seal indicator 316 as described herein that is different from the first indicator state.

Referring now to FIGS. 6 and 7, another sterilization container with a different closure mechanism will be described, according to an exemplary embodiment of the present subject matter. Like the sterilization containers 300 described with respect to FIGS. 1-3, the exemplary sterilization container 400 of FIGS. 6 and 7 includes multiple latches for applying force to the container gasket at more locations than typical sterilization containers, which helps provide a better seal between the container lid and body. More particularly, FIG. 6 provides a perspective view of the sterilization container 400 in a closed configuration, and FIG. 7 provides an exploded perspective view of the sterilization container 400. The depicted sterilization container 400 comprises a body 402 and a cover or lid 404. The body 402 and lid 404 together define an interior 406 of the sterilization container 400. One or more articles, e.g., clamps, scalpel blade handles, retractors, forceps, scissors, surgeon's towels, basins, and like surgical devices, instruments, or supplies, may be placed in the interior 406 of the container 400 for sterilization such that the article(s) may be reused in another procedure. It will be appreciated that the sterilization container 400 may generally have the form of a parallelepipedal box shape as shown in FIGS. 6 and 7, and the container 400 may have any appropriate size for containing the article(s) to be sterilized.

As shown in FIG. 6, to sterilize the article(s) in the container interior 406, and to maintain the sterility of such article(s) after sterilization, the lid 404 may be secured to the body 402 such that the container 400 is sealed against an ingress of contaminants. More specifically, the body 402 includes an open top portion 408 (FIG. 7), but when the lid 404 is secured to the body 402 as shown in FIG. 6, the lid 404 covers the open top portion 408 of the body 402 and a gasket 410 is compressed between the lid 404 and body 402 to seal the container 400 against the ingress of contaminants, as described in greater detail herein.

As shown in FIGS. 6 and 7, the lid 404 is retained on the body 402 by one or more latch assemblies 412. The latch assemblies 412 form a closure mechanism for securing the lid 404 to the body 402 and sealing the container interior 406, and the latch assemblies 412 are described in greater detail herein. Further, the container 400 includes one or more handles 414 for lifting, carrying, or otherwise handling the container 400. For example, a first handle 414 may be attached to a first end 402a of the body 402, and a second handle 414 may be attached to a second end 402b of the body 402, where the second end 402b is opposite the first end 402a. In other embodiments, a first handle 414 may be attached to a first side 402c of the body 402, and a second handle 414 may be attached to a second side 402d of the body 402, where the second side 402d is opposite the first side 402c and the first and second sides 402c, 402d extend between the first and second ends 402a, 402b. Other configurations and/or placements of one or more handles 414 may be used as well.

As further depicted in FIGS. 6 and 7, the container 400 may include a visual seal indicator 416 that provides a visual indication of a seal state of the sterilization container 400. For instance, the seal indicator 416 has a first indicator state and a second indicator state. In the first indicator state, the seal indicator 416 indicates to a user of the container 400 that the container 400 is in a first, unsealed state, where the container 400 is not sealed against the ingress of contaminants (i.e., contaminants could enter the container 400). In the second indicator state, the seal indicator 416 indicates to the user that the container 400 is in a second, sealed state, where the container 400 is sealed against the ingress of contaminants (i.e., contaminants cannot enter the container 400). That is, the seal indicator 416 is a binary indicator of the integrity of the seal between the body 402 and lid 404 of the container 400, e.g., the indicator 416 indicates when the seal is established and when the seal is broken or otherwise comprised. As described herein, the seal indicator 416 is unaffected by the sterilization modality to which the container 400 is subjected to sterilize the articles within the container 400. The seal indicator 416 is described in greater detail herein.

Moreover, as shown in FIG. 6, in some embodiments the lid 404 defines one or more vents 418 in a top surface 405 of the lid 404. In other embodiments of the lid 404, the lid 404 does not define vents 418 in the top surface 405, but the vent(s) 418 are defined elsewhere in the container 400, e.g., in one or more side surfaces 407 of the lid 404 that are generally orthogonal to the top surface 405, in the body 402, or in both the lid 404 and the body 402. The vent(s) 418 permit fluids, such as air, steam, and chemical sterilization agents and/or other sterilants, to pass through the lid 404 and into the interior 406 of the sterilization container 400, e.g., to sterilize the contents of the container 400, as well as to pass from the interior 406 to an exterior environment, e.g., to help the contents of the container 400 dry after a sterilization process.

A filter 420 is positioned within the sterilization container 400 adjacent the vent(s) 418 to prevent contaminants from entering the interior 406. For example, the filter 420 may be a sheet of material that extends over the open top portion 408 of the body 402 such that the filter is positioned between the lid 404 and the container interior 406. Another example is illustrated in FIG. 7, where a filter 420, configured as a sheet of material, is disposed adjacent each of two sets of vents 418, i.e., two filters 420 are included in the container 400, as well as a filter retainer or cover 421 on the opposite side of the filters 420 from the lid 404, e.g., to keep the filters 420 in position with respect to the vents 418. However, the filter(s) 420 need not be configured as a sheet but may have any suitable configuration or construction. Further, the filter(s) 420 can be made from a number of materials, such as a material from one of two main classes, reusables and disposables, which are described above with respect to FIGS. 1-3 in greater detail. Whatever materials are chosen, the resultant filter material must be compatible with the particular sterilization technique being used and must also provide both strength and barrier properties to maintain the sterile nature of the contents of the sterilization container 400 until use. In some embodiments, the lid 404 may define a window through which the filter 420 or filters 420 are visible to a user of the container 400, and the filter may also define a window, formed from a transparent breathable film or the like that still provides a barrier against contaminants, such that the user can see through the filter(s) 420 and into the interior 406 of the container 400 (e.g., in embodiments without filter retainer or cover 421 or in which a window also is defined in the cover 421) such that the user can view any articles, other indicators, or the like within the container 400 as described herein. However, in other embodiments, the filter(s) 420 may be made from a translucent or opaque material, such as, e.g., an SMS material, polytetrafluoroethylene (PTFE), paper, or the like. For example, polyolefin-based fibers and their resultant nonwovens are particularly well-suited for the production of a flexible filter 420, and a polypropylene spunbonded nonwoven can be used to impart strength characteristics to the filter 420. In some embodiments, the filter 420 may be made from laminates such as a laminate of spunbonded and meltblown or spunbonded, meltblown, spunbonded (SMS) to impart both strength and barrier properties to the filter. SMS materials are described above in greater detail. In an exemplary embodiment, the filter 420 or filters 420 are made from an SMS material, but the filter(s) 420 also may be made from other suitable materials.

As previously stated, the sterilization container 400 includes latch assemblies 412 for securing the lid 404 to the body 402 and ensuring the gasket 410 is properly compressed to seal the container interior 406 against the ingress of contaminants. In the exemplary embodiment of FIGS. 6 and 7, the sterilization container 400 includes four latch assemblies 412, one at each end 402a, 402b and side 402c, 402d of the body 402. In other embodiments, the sterilization container 400 includes any number greater than two of latch assemblies 412.

As shown in the depicted exemplary embodiment, each latch assembly 412 comprises a first latch member 422, a second latch member 424, a catch 426, a pair of pin supports 428, and a pair of pins 430. The first latch member 422 is attached or connected to the second latch member 424 such that the first latch member 422 is in operable communication with the second latch member 424 via the pins 430. More particularly, a first pin 430 extends through a first side 432 of the first latch member 422 and into a first side 434 of the second latch member 424, and a second pin 430 extends through a second side 436 of the first latch member 422 and into a second side 438 of the second latch member 424. Each pin 430 also extends within a pin support 428, which is attached to the body 402, thereby securing the first and second latch members 422, 424 to the container body 402.

A user manipulates the first latch member 422 to pivot the second latch member 424 into and out of the catch 426 to latch and unlatch the lid 404 with respect to the body 402. For example, from the closed position shown in FIG. 6, a user may grasp the first latch member 422 and pivot or rotate the first latch member 422 upward to loosen or "pop" the second latch member 424 from the catch 426, which is defined in the lid 404 in the depicted embodiment. Once all four second latch members 424 are loosened with respect to their catches 426, the lid 404 is no longer secured to the body 402 and the lid 404 may be removed therefrom. To secure the lid 404 with respect to the body 402, a first end 440 of each second latch member 424 is positioned at its respective catch 426. When the user pushes on a first latch member 422, the first latch member 422 pivots or rotates downward, pulling the associated second latch member 424 into engagement with its catch 426. When all four first latch members 422 are pivoted or rotated downward against their respective body end 402a, 402b or side 402c, 402d, the lid 404 is secured with respect to the body 402, and the gasket 420 is compressed to seal the interior 406 against the ingress of contaminants. It will be appreciated that each of the first and second latch members 422, 424 pivots or rotates about the pins 430 that attach or connect the respective latch members 422, 424.

Although described herein as secured to the container body 402 and engaging a catch 426 on the lid 404, in other embodiments, the latch assemblies 412 may be reversed. That is, the first and second latch members 422, 424 may be secured (via pins 430 and pin supports 428 or another suitable mechanism) to the lid 404. In such embodiments, the catch 426 is defined or included on the body 402, and the second latch member 424 pivots or rotates downward to engage the catch 426, with the first latch member 422 pivoting or rotating upward to secure the second latch member 424 in the catch 426, and the first latch member 422 pivots or rotates downward to loosen the second latch member 424 from the catch 426.

The visual seal indicator 416 of the sterilization container 400 may be configured as any of the seal indicators described herein. For example, the seal indicator 416 may be configured as a plunger-type indicator assembly, such as one of indicator assemblies 40, 130, or 280, or as a deformable gasket-type indicator assembly, such as indicators 20 or 316. No matter its configuration, the seal indicator 416 provides a visual indication of a seal state of the sterilization container 400. For instance, the seal indicator 416 indicates to a user of the container 400 whether the container 400 is in a first, unsealed state, where the container 400 is not sealed against an ingress of contaminants (i.e., contaminants could enter the container 400), or a second, sealed state, where the container 400 is sealed against the ingress of contaminants (i.e., contaminants cannot enter the container 400). That is, the seal indicator 416 is a binary indicator of the integrity of the seal between the body 402 and lid 404 of the container 400, e.g., the indicator 416 indicates when the seal is established and when the seal is broken or otherwise compromised. More particularly, the seal indicator 416 has a first indicator state, in which the seal indicator 416 displays a first indicium to indicate to a user that the container is in its unsealed state, and a second indicator state, in which the seal indicator 416 displays a second indicium to indicate to the user that the container is in its sealed state. The seal indicator 416 is visible to a user of the container 400 from the exterior of the container 400 to signal to the user whether the container is sealed or unsealed. A change in state, i.e., from the first indicator state to the second indicator state or from the second indicator state to the first indicator state, may be achieved by a change in color, shape, size, position, etc. of the seal indicator 416 to signal the container 400 has transitioned from its unsealed state to its sealed state or from its sealed state to its unsealed state.

Accordingly, the sterilization container 400 described with respect to FIGS. 6 and 7 provides improved sealing between the lid 404 and body 402, as well as an indication of the state of the seal, i.e., of the integrity of the seal. For instance, by providing at least one latch assembly 412 on each end 402a, 402b and side 402c, 402d, more force or pressure is applied to the container gasket 410 to ensure a good seal between the body 402 and lid 404. Further, the latch assemblies 412 may be sized, shaped, and positioned to maximize their effectiveness in applying force or pressure on the gasket 410. That is, the latch assemblies 412, particularly the second latch members 424, may be configured to apply force or pressure to the gasket 410 at a certain location, over a minimum length, etc. to more evenly distribute the force or pressure applied to the gasket 410, to apply a sufficient sealing force to the gasket 410, etc. Moreover, the seal indicator 416 may be selected and positioned to reliably indicate to a user of the container 400 whether the interior 406 of the container 400 is sealed against the ingress of contaminants. Of course, other benefits and advantages also may be realized from the subject matter discussed with respect to FIGS. 6 and 7.

Turning now to FIG. 8, in some embodiments of sterilization containers, the seal may have a maze configuration. That is, a tortuous path is formed from the container interior to the container exterior at the interface between the container lid and container body, e.g., to decrease the likelihood that contaminants will enter the interior of the container. For example, as described with respect to FIG. 8, the sterilization container 400 described with respect to FIGS. 6 and 7 may include a maze seal 450. A portion of a latch assembly 412 is illustrated in FIG. 8; the first latch member 422 is omitted for clarity.

As shown in FIG. 8, a body interface feature 452 is provided along the upper perimeter of the body 402, i.e., along a rim 409 at the open top portion 408 of the body 402. A lid interface feature 454 is provided along the outer edge 403 of the lid 404. Although shown as separate pieces attached to the body 402 and lid 404, in other embodiments, the body interface feature 452 may be integral with the body 402 and the lid interface feature 454 may be integral with the lid 404. For example, the body interface feature 452 and the body 402 may be formed as a single piece, and the lid interface feature 454 and the lid 404 may be formed as a single piece.

Each interface feature 452, 454 defines a series of channels such that the body interface feature 452 meshes with the lid interface feature 454 to form a tortuous path from the environment external to the container 400 to the container interior 406. More particularly, the body interface feature 452 includes body channel segments 456; in the depicted embodiment, the body interface feature 452 includes three body channel segments: first segment 456a, second segment 456b, and third segment 456c. Further, body channels 458 are defined between the body channel segments 456. A first body channel 458a is defined between the first body channel segment 456a and the second body channel segment 456b, and a second body channel 458b is defined between the second body channel segment 456b and the third body channel segment 456c. Similarly, the lid interface feature 454 includes lid channel segments 460, and in the illustrated embodiment, the lid interface feature 454 includes four lid channel segments: first segment 460a, second segment 460b, third segment 460c, and fourth segment 460d. The first and fourth lid channel segments 460a, 460d flank the body interface feature 452, such that the body interface feature 452 fits within the lid interface feature 454. Moreover, lid channels 462 are defined between the lid channel segments 460. A first lid channel 462a is defined between the first lid channel segment 460a and the second lid channel segment 460b, a second lid channel 462b is defined between the second lid channel segment 460b and the third lid channel segment 460c, and a third lid channel is defined between the third channel segment 460c and the fourth lid channel segment 460d.

As shown in FIG. 8, the body channel segments 456 fit within the lid channels 462, and the second and third lid channel segments 460b, 460c fit within the body channels 458, with the first and fourth lid channel segments 460a, 460d extending along an inner surface 452a and an outer surface 452b, respectively, of the body interface feature 452. Further, the first lid channel segment 460a is longer than the other lid channel segments 460, extending downward along the inner surface 452a of the body interface feature 452 beyond the bottom of the body channels 458.

As further illustrated in FIG. 8, a gasket 464 is positioned at the bottom of each lid channel 462 such that the gaskets 464 may be compressed between the body 402 and lid 404 of the container 400 when the lid 404 is secured to the body 402. Together with the multiple channel segments 456, 460, channels 458, 462, and lengthened inner or first lid channel segment 460a, the gaskets 464 help prevent contaminants from the external environment from entering the container interior 406. More particularly, the interface between the lid 404 and the body 402 provides a location for contaminants to enter the container interior 406 after the container contents have been sterilized and thereby compromise the sterility of the articles in the container 400. The series of channel segments 456, 460 received in channels 458, 462, or the intermeshing of the body interface feature 452 with the lid interface feature 454, creates a tortuous path at the body-lip interface for contaminants to traverse to enter the container interior 406, thus discouraging contaminants from entering the interior 406. Further, the series of gaskets 464 help stop contaminants from advancing through the maze seal 450 along the tortuous path, e.g., by blocking the contaminants on the exterior side of the container 400. Accordingly, while either the intermeshed interface features 452, 454 or the gaskets 464 would, on their own, help prevent contaminants from advancing into the interior 406, the combination of the intermeshed interface features 454, 454 and gaskets 464 provide enhanced protection and/or layers of protection such that the container interior 406 may be protected against contamination even if one or more layers of protection are breached.

It will be appreciated that the maze seal 450 may have other configurations as well. For example, a different number of body channels 458 and lid channels 460 may be defined by a different number of body channel segments 456 and lid channel segments 460. As another example, the lid interface feature 454 may be received within the body interface feature 452, where the body interface feature 452 includes one more channel segment 456 than the lid interface feature 454 such that a body channel segment 456 extends along the inner and outer surfaces of the lid interface feature 454. Additionally, in such embodiments, the body interface feature 452 would define one more channel 458 than the lid interface feature 454. Further, the gaskets 464 may be positioned in the bottom of the body channels 458 rather than in the bottom of the lid channels 462 as shown in FIG. 8. Still further, the channels 458, 462 and gaskets 464 may have a different cross-sectional shape than as illustrated in FIG. 8. For instance, although shown with generally round or circular cross-sectional shapes, the cross-sections may be generally square or any other suitable shape.

Additionally, the maze seal 450 may be used with any appropriate sterilization container and, thus, may be used in conjunction with a separate seal indicator. However, in some embodiments, the maze seal 450 also may incorporate a visual seal indicator 416. For example, as described above with respect to some embodiments of the visual seal indicator 316, at least the lid interface feature 454 may be formed from a transparent material, such as high temperature resistant Radel® PPSU, and the gaskets 464 may be visible through the lid interface feature 454. More particularly, the gaskets 464 contact an inner surface 466 of the lid interface feature 454 when the lid 404 is secured to the body 402 and the gaskets 464 are sufficiently compressed to seal the container interior 406. When the gaskets 464 contact the inner surface 466, there is a visible change at the lid interface feature 454. For example, the gaskets 464 may be yellow and the transparent lid interface feature 454 may be tinted blue such that when the yellow gaskets 464 contact the transparent blue lid interface feature 454, green stripes (or other markings) that extend around the perimeter of the lid 404 are visible at the lid interface feature 454. Thus, the visual seal indicator provided by the maze seal 450 is visible from all sides of the container 400. Of course, other color combinations or other visual state changes, such as changes in pattern, shape, and/or size as described herein, may be used as well. Accordingly, the maze seal 450 may provide be an indicator of the seal state of the container 400, where the first indicator state is when the gaskets 464 are not in contact with the lid interface feature 454, which is signaled by any appropriate visual state of the seal indicator 416 as described herein (e.g., the lid interface feature 454 appears only blue). The second indicator state is when the gaskets 464 are in contact with the lid interface feature 454, which is signaled by any appropriate visual state of the seal indicator 416 as described herein that is different from the first indicator state (e.g., lid interface feature 454 appears blue with green stripes).

Accordingly, the maze seal 450 described with respect to FIG. 8 provides improved sealing between the lid 404 and body 402, as well as an indication of the state of the seal, i.e., of the integrity of the seal between the body 402 and lid 404. For instance, by providing intermeshing segments and gaskets along the interface between the body 402 and lid 400 of the container 400, the maze seal 450 creates a tortuous path that contaminants must traverse to enter the container interior 406, thereby reducing the opportunity of contaminant breach (by bacteria or the like). Moreover, the maze seal 450 may be configured to include the seal indicator 416 to indicate to a user of the container 400 whether the interior 406 of the container 400 is sealed against the ingress of contaminants. However, the maze seal 450 also may be used with other sterilization container embodiments, including such embodiments that provide other means for indicating the integrity of the seal between the container body and lid. Further, other benefits and advantages also may be realized from the subject matter discussed with respect to FIG. 8.

Turning now to FIGS. 9 through 12, another sterilization container 500 will be described, according to an exemplary embodiment of the present subject matter. The sterilization container 500 comprises a body 502 and a lid or cover 504 that together define an interior 506 of the sterilization container 500. One or more articles, e.g., clamps, scalpel blade handles, retractors, forceps, scissors, surgeon's towels, basins, and like surgical devices, instruments, or supplies, may be placed in the container interior 506 for sterilization such that the article(s) may be reused in another procedure. It will be appreciated that the sterilization container 500 may generally have the form of a parallelepipedal box shape as shown in FIGS. 9-12, and the container 500 may have any appropriate size for containing the article(s) to be sterilized. Further, it will be understood that the sterilization container 500, particularly the body 502, may be configured similarly to the other exemplary sterilization containers described herein. However, the lid 504 and closure mechanism embody differences from others described herein.

As shown in FIG. 9, to sterilize the article(s) in the container interior 506, and to maintain the sterility of such article(s) after sterilization, the lid 504 may be secured to the body 502 such that the container 500 is sealed against an ingress of contaminants. More specifically, the body 502 includes an open top portion 508 (FIG. 10), but when the lid 504 is secured to the body 502 as shown in FIG. 9, the lid 504 covers the open top portion 508 of the body 502 and a gasket 510 is compressed between the lid 504 and body 502 to seal the container 500 against the ingress of contaminants, as described in greater detail herein.

As shown in FIGS. 9-12, the lid 504 is retained on the body 502 by one or more latch assemblies 512. The latch assemblies 512 are described in greater detail herein. Further, the container 500 includes one or more handles 514 for lifting, carrying, or otherwise handling the container 500. For example, a first handle 514 may be attached to a first end 502a of the body 502, and a second handle 514 may be attached to a second end 502b of the body 502, where the second end 502b is opposite the first end 502a. In other embodiments, a first handle 514 may be attached to a first side 502c of the body 502, and a second handle 514 may be attached to a second side 502d of the body 502, where the second side 502d is opposite the first side 502c and the first and second sides 502c, 502d extend between the first and second ends 502a, 502b. Other configurations and/or placements of one or more handles 514 may be used as well.

As further depicted in FIGS. 9-12, the container 500 may include a visual seal indicator 516 that provides a visual indication of a seal state of the sterilization container 500. For instance, the seal indicator 516 has a first indicator state and a second indicator state. In the first indicator state, the seal indicator 516 indicates to a user of the container 500 that the container 500 is in a first, unsealed state, where the container 500 is not sealed against the ingress of contaminants (i.e., contaminants could enter the container 500). In the second indicator state, the seal indicator 516 indicates to the user that the container 500 is in a second, sealed state, where the container 500 is sealed against the ingress of contaminants (i.e., contaminants cannot enter the container 500). That is, the seal indicator 516 is a binary indicator of the integrity of the seal between the body 502 and lid 504 of the container 500, e.g., the indicator 516 indicates when the seal is established and when the seal is broken or otherwise comprised. As described herein, the seal indicator 516 is unaffected by the sterilization modality to which the container 500 is subjected to sterilize the articles within the container 500. The seal indicator 516 is described in greater detail herein.

Moreover, as shown in FIGS. 9-12, the lid 504 and a filter 520 define one or more vents 518 of the sterilization container 500. In other embodiments of the container 500, the vent(s) 518 may be defined as shown in other embodiments, e.g., as openings 518 in a top surface 505 of the lid 504; as openings 518 in one or more side surfaces 507 of the lid 504, where the side surfaces 507 are orthogonal to the top surface 504; as openings 518 in the body 502; or as openings 518 in both the lid 504 and the body 502. The vent(s) 518 and filter 520 permit fluids, such as air, steam, and chemical sterilization agents and/or other sterilants, to pass through the lid 504 and into the interior 506 of the sterilization container 500, e.g., to sterilize the contents of the container 500, as well as to pass from the interior 506 to an exterior environment, e.g., to help the contents of the container 500 dry after a sterilization process. As illustrated, for example, in FIG. 9, the filter 520 is disposed between the lid 504 and the body 502 such that the lid 504 is spaced apart from the body 502 (except for the latch assemblies 512, as described in greater detail herein). As such, the filter 520 is directly exposed to the environment external to the container 500. That is, spacing the lid 504 from the body 502 creates spaces that define the vents 518, and the filter 520 is disposed within the spaces to provide a barrier between the external environment and the container interior 506.

The filter 520 can be made from a number of materials, such as a material from one of two main classes, reusables and disposables, which are described above with respect to FIGS. 1-3 in greater detail. Whatever materials are chosen, the resultant filter material must be compatible with the particular sterilization technique being used and must also provide both strength and barrier properties to maintain the sterile nature of the contents of the sterilization container 500 until use. In some embodiments, the lid 504 may be transparent or may define a window 519 through which a user of the sterilization container 500 can view the container interior 506 and, thus, the contents of the container 500, such as any articles, indicators, or the like as described herein. The filter 520 adjacent the lid 504 likewise may define a window, formed from a transparent breathable film or the like that still provides a barrier against contaminants, such that the user can see through the filter 520 and into the interior 506. However, in other embodiments, the filter 520 may be made from a translucent or opaque material, such as, e.g., an SMS material, polytetrafluoroethylene (PTFE), paper, or the like. For example, polyolefin-based fibers and their resultant nonwovens are particularly well-suited for the production of a flexible filter 520, and a polypropylene spunbonded nonwoven can be used to impart strength characteristics to the filter 520. In some embodiments, the filter 520 may be made from laminates such as a laminate of spunbonded and meltblown or spunbonded, meltblown, spunbonded (SMS) to impart both strength and barrier properties to the filter. SMS materials are described above in greater detail. In an exemplary embodiment, the filter 520 is made from an SMS material, but the filter 520 also may be made from other suitable materials.

Further, in the depicted exemplary embodiment, the gasket 510 and filter 520 are integrally formed as a single piece component, which may be referred to herein as a combination gasket/filter 522. A combination gasket/filter 622 according to another exemplary embodiment of the present subject matter is described herein with respect to FIGS. 13-16. In some embodiments, the gasket 510 of the combination gasket/filter 522 forms the outermost boundary of the combination gasket/filter 522. In such embodiments, the gasket portion 510 of the combination gasket/filter 522 may be wider than typical sterilization container gaskets, and as shown in FIG. 10, the lip 509 (i.e., the portion of the body 502 against which the gasket portion 510 rests) also may be wider than normal. As such, the body 502 and the gasket portion 510 of the gasket/filter 522 have an increased contact area compared to typical sterilization containers, thereby forming a more tortuous path for contaminants to enter the container interior 506.

Further, because the combination gasket/filter 522 is formed as a single piece component, even when including a transparent film to form a window into the interior 506, and the gasket/filter 522 completely covers the open top end 508 of the body 502 as shown in the figures, interfaces between mating parts can be minimized. For example, a combination gasket/filter eliminates separate interfaces between the lid 504 and filter 520 and the lid 504 and gasket 510. Minimizing the number of interfaces helps reduce the opportunity for contamination breach, i.e., a breach of the seal by bacteria or other organisms or substances that could compromise the sterility and safety of the articles within the container 500. Further, the combination gasket/filter 522 allows for a single use gasket 510, which eliminates wear and tear to the gasket 510 that arises from reusing the gasket in additional opening/closing cycles and sterilization cycles. That is, it may be desirable for the gasket/filter 522 to be a disposable, single use component of the container 500, e.g., to reduce the opportunity for seal breach due to wear of the gasket 510. As illustrated in FIG. 10, in some embodiments the lid 504 also may be configured to be disposable, such that a new, single use lid and gasket/filter assembly is used with a reusable body 502 each time the container 500 is used to sterilize one or more articles. Moreover, the single piece gasket/filter 522 simplifies assembly and use by a user of the container 500. For example, a single piece gasket/filter 522 is easier to assemble with the body 502 and lid 504 than a separate gasket and one or more filters, which also could require filter retainers or the like to hold them in position. Thus, the reduced number of parts helps simplify assembly of the container 500. Similarly, a single piece gasket/filter 522 is easier to remove than multiple pieces, thereby simplifying the opening of the container 500.

As previously stated, the sterilization container 500 includes latch assemblies 512 forming a closure mechanism for securing the lid 504 to the body 502 and ensuring the gasket 510 is properly compressed to seal the container interior 506 against the ingress of contaminants. In the exemplary embodiment of FIGS. 9-12, the sterilization container 500 includes four latch assemblies 512, one at each end 502a, 502b and side 502c, 502d of the body 502. In other embodiments, the sterilization container 500 includes any suitable number of latch assemblies 512.

As shown in FIGS. 9-12, the latch assemblies 512 include a first end latch assembly 512a, a second end latch assembly 512b, a first side latch assembly 512c, and a second side latch assembly 512d. Three of the four latch assemblies 512 are configured very similarly and, if not identical, are nearly identical. The fourth latch assembly 512 is similar but has one particular difference, a handle, which could be incorporated into any of the other latches 512. More particularly, each latch assembly 512 includes an arm 524 that extends downward from the lid 504 toward the container body 502. That is, a first arm 524a extends downward from a first end 504a of the lid 504, a second arm 524b extends downward from a second end 504b of the lid 504, a third arm extends downward from a first side 504c of the lid 504, and a fourth arm extends downward from a second side 504d of the lid 504. On each arm 524, a projection 526 extends inward toward the container body 502 from a distal end 524a of the arm 524. Each projection 526 engages a catch 528, such as a lip 509 defined along the open top portion 508 of the body 502, to secure the lid 504 to the body 502. The first side latch assembly 512c, which is the fourth, different latch assembly 512 as shown in FIG. 9, also includes a handle 530 that is integrally formed with the arm 524 of the first side latch assembly 512c. As shown, for example, in FIG. 12, the user may grasp the handle 530 to unlatch the latch assemblies 512, first by disengaging the projection 526 of the first side latch assembly 512c from its catch 528. Then, as the user continues to lift the lid 504 away from the body 502, the remaining projections 526 are disengaged from their respective catches 528 to remove the lid 504 from the body 502. As illustrated in FIG. 12, the end latch assemblies 512a, 512b, which are disposed between the side latch assemblies 512c, 512d, may be disengaged after the first side latch assembly 512c, and the second side latch assembly 512d, which is opposite the first side latch assembly 512c, may be disengaged last. The handle 530 and arm 524 provide an area 532 for attaching or securing a label that, e.g., specifies the contents of the container 500, the date and time of sterilization, and/or other pertinent information, or a way to access such information, such as a radio-frequency identification (RFID) tag, a barcode, a matrix or two-dimensional barcode (or Quick Response (QR) code), or other appropriate means for accessing such information.

As depicted in the exemplary embodiment shown in FIGS. 9-12, the arm 524 of each latch assembly 512 may extend along a majority of the respective lid end 504a, 504b or lid side 504c, 504d from which the arm 524 depends. More specifically, each arm 524 has a length such that the arm 524 extends along the majority of the portion of the lid 504 from which the respective arm 524 depends. Each projection 526 may extend over the length of the arm 524 on which the projection 526 is defined, or the projection may extend along only a portion of the length of the arm 524 on which the projection 526 is defined. Alternatively, each arm 524 may define a plurality of projections 526 along the length of the arm 524. As described herein with respect to other sterilization container embodiments, the distribution of the latch assemblies 512 about the perimeter of the container 500, as well as the length of the arms 524, provides a more even pressure distribution along the gasket 510 than typical sterilization containers, which generally include one latch on each end of the container. That is, the multiple latch assemblies 512 spaced about the perimeter of the sterilization container 500 provide several more locations than typical containers where force is applied to keep the lid 504 secured to the body 502. Further, when the projections 526 engage their catches 528, the arms 524 distribute the applied pressure or force along their length, which helps more evenly compress the gasket 510 between the lid 504 and body 502. A more evenly distributed force or pressure on the gasket 510 provides a better seal, helping to prevent the ingress of contaminants to the container interior 506, e.g., by resisting loss of the seal over time. For instance, with additional latch assemblies 512 having arms 524 that distribute the sealing pressure, the seal can be maintained even if one or more latch assemblies 512 loosen (or apply less force) over time. Of course, other advantages and benefits also may be realized from the closure mechanism described with respect to FIGS. 9-12.

As shown in the exemplary embodiment, the visual seal indicator 516 may be incorporated into the filter 520. The seal indicator 516 may be configured similarly to the deformable gasket-type indicator assemblies described herein, such as indicators 20 or 316, which extends around the perimeter of the container 500 and is visible from all sides of the container 500, or the indicator 516 may have a different configuration. For example, the seal indicator 516 may be a compressible feature of the filter 520 configured like the gasket seal indicator 316 of FIGS. 4 and 5, comprising along the vertical direction V a top portion, a middle portion, and a bottom portion. The middle portion is compressible such that the top portion meets the bottom portion when the seal indicator 516 is compressed in the sealed state, revealing an indicium of the sealed state as described in greater detail herein. When the seal indicator 516 is not compressed, e.g., when the lid 504 is not secured to the body 502, the middle portion is uncompressed and, thus, visible to the user through the latch assemblies 512 and at the vents 518. Of course, the seal indicator 516 may have other configurations as well, e.g., the seal indicator 516 may be formed from a compressible material that changes from one color to another when compressed, or the container 500 may include a seal indicator that is configured as a plunger-type indicator assembly, such as one of indicator assemblies 40, 130, or 280.

As previously stated, the seal indicator 516 provides a visual indication of the seal state of the sterilization container 500. More particularly, the seal indicator 516 has a first indicator state that indicates the unsealed container state and a second indicator state that indicates the sealed container state. The seal indicator 516 is visible to a user of the container 500 from the exterior of the container 300 to signal to the user whether the container 500 is sealed or unsealed. A change in state, i.e., from the first indicator state to the second indicator state or from the second indicator state to the first indicator state, may be achieved by a change in color, shape, size, position, etc. of the seal indicator 516 to signal the container 500 has transitioned from its unsealed state to its sealed state or from its sealed state to its unsealed state. Thus, when the gasket 510 is not compressed, or not fully compressed, such that the interior 506 is not sealed against the ingress of contaminants, the container 500 is in its first, unsealed state and the seal indicator 516 is in its first indicator state. Similarly, when the gasket 510 is fully compressed, such that the interior 506 is sealed against the ingress of contaminants, the container 500 is in its second, sealed state and the seal indicator 516 transitions from its first indicator state to its second indicator state. Other means for indicating the seal state of the container 500 or the integrity of the gasket 510, e.g., auditory or other non-visual indicators, may be used as well.

As described with respect to other embodiments, the seal indicator 516 is configured to display a first indicium 516a in the first indicator state and is configured to display a second indicium 516b in the second indicator state. In an exemplary embodiment, the first indicium 516a is a first color or hue and the second indicium 516b is a second color or hue, and the first and second colors/hues may be selected such that there is a high contrast between the colors/hues and/or between the colors/hues and the sterilization container 500, and/or the colors/hues may be selected to reinforce the signal communicated by the color or hue. For example, in an exemplary embodiment, the first color is red to indicate the container 500 is unsealed (i.e., contaminants could enter the container 500 and reach any articles in the interior 506), and the second color is green to indicate the container 500 is sealed (i.e., contaminants cannot enter the container 500 and any articles in the container 500 would remain sterile after sterilization). In another exemplary embodiment, in the first indicator state (when the container 500 is unsealed), no separate indicium may be displayed or the first indicium 516a may be the same color as the filter media 520 of the combination gasket/filter 522, e.g., the combination gasket/filter 522 may be all one color as shown in FIGS. 10-12. In such embodiments, the seal indicator 516 displays the second indicium 516b in the second indicator state (when the container 500 is sealed), and the second indicium 516b may be a different color or hue from the filter media 520, e.g., a high contrast color from the color of the filter media 520, as shown in FIGS. 9 and 11. Thus, the seal indicator 516 is configured to display a first color or hue when the container 500 is unsealed and a second color or hue when the container 500 is sealed, such that the seal indicator 516 indicates a change in the seal state of the container 500 through a change in color. In other embodiments, other visual indicia, such as patterns, images, and/or words, may be used instead of or in conjunction with colors to indicate the container seal state and the integrity of the gasket 510.

As depicted most clearly in FIGS. 9 and 10, the seal indicator 516 extends about the entire perimeter of the filter 520 such that the seal indicator 516 is visible from the container exterior on all sides of the container 500. That is, the seal indicator 516 is visible from each of the first end 502a, the second end 502b, the first side 502c, and the second side 502d of the body 502. Further, at least the arms 524 of the latch assemblies 512 are formed from a transparent material, as shown in FIGS. 9-11, such that the seal indicator 516 is visible through the arms 524. In some embodiments, the entire lid 504 may be formed from a transparent material such that the entire gasket/filter 522, including the seal indicator 516, is visible from the exterior of the container 500, including through the top surface 505 of the lid 504.

Accordingly, the sterilization container 500 described with respect to FIGS. 9-12 provides improved sealing between the lid 504 and body 502, as well as a simple means for opening the container 500 and an indication of the state of the seal, i.e., of the integrity of the seal between the lid 504 and body 502. For instance, by providing at least one latch assembly 512 on each end 502a, 502b and side 502c, 502d, more force or pressure is applied to the container gasket 510 to ensure a good seal between the body 502 and lid 504. Further, the latch assemblies 512 may be sized, shaped, and positioned to maximize their effectiveness in applying force or pressure on the gasket 510. That is, the latch assemblies 512, particularly the arms 524, may be configured to apply force or pressure to the gasket 510 at a certain location, over a minimum length, etc. to more evenly distribute the force or pressure applied to the gasket 510, to apply a sufficient sealing force to the gasket 510, etc. Additionally, at least one latch assembly 512 includes a handle 530 for easily disengaging, e.g., with one hand as shown in FIG. 12, the latch assemblies 512 and opening the container 500. Moreover, the seal indicator 516 may be selected and positioned to reliably indicate to a user of the container 500 whether the interior 506 of the container 500 is sealed against the ingress of contaminants. Of course, other benefits and advantages also may be realized from the subject matter discussed with respect to FIGS. 9-12.

Turning now to FIGS. 13 through 16, another sterilization container 600 will be described, according to an exemplary embodiment of the present subject matter. The sterilization container 600 comprises a body 602 and a lid or cover 604. As described herein, the body 602 and lid 604 or body 602 and a combination gasket/filter 622 together define an interior 606 of the sterilization container 600. One or more articles, e.g., clamps, scalpel blade handles, retractors, forceps, scissors, surgeon's towels, basins, and like surgical devices, instruments, or supplies, may be placed in the container interior 606 for sterilization such that the article(s) may be reused in another procedure. It will be appreciated that the sterilization container 600 may generally have the form of a parallelepipedal box shape as shown in FIGS. 13-16, and the container 600 may have any appropriate size for containing the article(s) to be sterilized.

Referring particularly to FIG. 14, the container 600 includes a filter 620 that comprises a gasket 610 for sealing the container interior 606 against the ingress of contaminants. That is, the gasket 610 and filter 620 are integrally formed as a single piece component, which may be referred to herein as a combination gasket/filter 622. As shown in FIG. 14, to sterilize the article(s) in the container interior 606, and to maintain the sterility of such article(s) after sterilization, the combination gasket/filter 622 may be secured to the body 602 such that the container 600 is sealed against an ingress of contaminants. More specifically, the body 602 includes an open top portion 608, but when the combination gasket/filter 622 is secured to the body 602 as illustrated in FIG. 13, the combination gasket/filter 622 covers the open top portion 608 of the body 602 to close the interior 606 and the gasket 610 of the combination gasket/filter 622 is compressed against the body 602 to seal the container 600 against the ingress of contaminants, as described in greater detail herein. The lid 604 fits over or around the combination gasket/filter 622, e.g., to provide additional rigidity and/or stiffness to the combination gasket/filter 622. Further, the lid 604 may protect the combination gasket/filter 622, e.g., at the corners, sides, and top edges of the gasket/filter 622, as well as a top surface 624 by providing a surface for stacking another sterilization container on top of the container 600 that is separate from the gasket/filter 622.

As shown in FIGS. 13-16, the combination gasket/filter 622 includes a plurality of gasket assemblies 612, which comprise the gasket 610. The gasket assemblies 612, which form a closure mechanism for sealing the container interior 606, are described in greater detail herein. Further, the container 600 includes one or more handles 614 for lifting, carrying, or otherwise handling the container 600. For example, a first handle 614 may be attached to a first end 602a of the body 602, and a second handle 614 may be attached to a second end 602b of the body 602, where the second end 602b is opposite the first end 602a. In other embodiments, a first handle 614 may be attached to a first side 602c of the body 602, and a second handle 614 may be attached to a second side 602d of the body 602, where the second side 602d is opposite the first side 602c and the first and second sides 602c, 602d extend between the first and second ends 602a, 602b. Other configurations and/or placements of one or more handles 614 may be used as well.

As further depicted in FIGS. 13-16, the container 600 may include a visual seal indicator 616 that provides a visual indication of a seal state of the sterilization container 600. For instance, the seal indicator 616 has a first indicator state and a second indicator state. In the first indicator state, the seal indicator 616 indicates to a user of the container 600 that the container 600 is in a first, unsealed state, where the container 600 is not sealed against the ingress of contaminants (i.e., contaminants could enter the container 600). In the second indicator state, the seal indicator 616 indicates to the user that the container 600 is in a second, sealed state, where the container 600 is sealed against the ingress of contaminants (i.e., contaminants cannot enter the container 600). That is, the seal indicator 616 is a binary indicator of the integrity of the seal between the body 602 and combination gasket/filter 622, e.g., the indicator 616 indicates when the seal is established and when the seal is broken or otherwise comprised. As described herein, the seal indicator 616 is unaffected by the sterilization modality to which the container 600 is subjected to sterilize the articles within the container 600. The visual indicator 616 is described in greater detail herein.

Moreover, as shown in FIGS. 13-16, the lid 604 defines one or more vents 618 through which the combination gasket/filter 622 is exposed. The vent(s) 618 and filter 620 of the gasket/filter 622 permit fluids, such as air, steam, and chemical sterilization agents and/or other sterilants, to pass through the lid 604 and into the interior 606 of the sterilization container 600, e.g., to sterilize the contents of the container 600, as well as to pass from the interior 606 to an exterior environment, e.g., to help the contents of the container 600 dry after a sterilization process. As illustrated, for example, in FIGS. 13 and 14, the filter 620 extends over the entire open top portion 608 of the body 602 to provide a barrier between the external environment and the container interior 606.

The filter 620 of the combination gasket/filter 622 can be made from a number of materials, such as a material from one of two main classes, reusables and disposables, which are described above with respect to FIGS. 1-3 in greater detail. Whatever materials are chosen, the resultant filter material must be compatible with the particular sterilization technique being used and must also provide both strength and barrier properties to maintain the sterile nature of the contents of the sterilization container 600 until use. As shown in FIGS. 13 and 14, the combination gasket/filter 622 defines a window 626 through which a user of the sterilization container 600 can view the container interior 606. Further, the lid 604 defines a window 628 through which the gasket/filter window 626 is visible; the lid 604 may include cross-members 628a across the window 628 to help provide rigidity and stability to the lid 604, e.g., when stacking sterilization container 600 with another container, without blocking the view through the window 628. The filter 620 may likewise define a window, formed from a transparent breathable film or the like that still provides a barrier against contaminants, such that the user can see through the filter 620 and into the interior 606 to view any articles, other indicators, or the like that are within the container 600. However, in other embodiments, the filter 620 may be made from a translucent or opaque material, such as, e.g., an SMS material, polytetrafluoroethylene (PTFE), paper, or the like. For example, polyolefin-based fibers and their resultant nonwovens are particularly well-suited for the production of a flexible filter 620, and a polypropylene spunbonded nonwoven can be used to impart strength characteristics to the filter 620. In some embodiments, the filter 620 may be made from laminates such as a laminate of spunbonded and meltblown or spunbonded, meltblown, spunbonded (SMS) to impart both strength and barrier properties to the filter. SMS materials are described above in greater detail. In an exemplary embodiment, the filter 620 is made from an SMS material, but the filter 620 also may be made from other suitable materials.

As described, the combination gasket/filter 622 is formed as a single piece component, even when including a window 626, and as shown in the figures, the gasket/filter 622 completely covers the open top end 608 of the body 602, both of which minimize interfaces between mating parts. Minimizing the number of interfaces helps reduce the opportunity for contamination breach, i.e., a breach of the seal by bacteria or other organisms or substances that could compromise the sterility and safety of the articles within the container 600. Further, the combination gasket/filter 622 allows for a single use gasket 610, which eliminates wear and tear to the gasket 610 that arises from reusing the gasket in additional opening/closing cycles and sterilization cycles. That is, it may be desirable for the gasket/filter 622 to be a disposable, single use component of the container 600, e.g., to reduce the opportunity for seal breach due to wear of the gasket 610. Moreover, the single piece gasket/filter 622 simplifies assembly and use by a user of the container 600. For example, a single piece gasket/filter 622 is easier to assemble with the body 602 and lid 604 than a separate gasket and one or more filters, which also could require filter retainers or the like to hold them in position. Thus, the reduced number of parts helps simplify assembly of the container 600. Similarly, a single piece gasket/filter 622 is easier to remove than multiple pieces, thereby simplifying the opening of the container 600.

As previously described, the gasket 610 of the combination gasket/filter 622 is part of a gasket assembly 612, which also includes the seal indicator 616, and a plurality of gasket assemblies 612 are provided with the gasket/filter 622 depicted in the exemplary embodiment. More particularly, each gasket assembly 612 comprises a gasket 610, which is an elastomeric band extending around the perimeter of the gasket/filter 622. When the elastomeric gasket 610 is tightened or stretched, the gasket 610 compresses the filter 620 against the container body 602, thereby creating a seal between the body 602 and gasket/filter 622. The elastomeric gasket 610 is surrounded by a non-elastic sheath 630 that does not tighten or stretch when the gasket 610 is tightened or stretched to compress against the body 602. The sheath 630 defines openings or slits 632 therein; the sheath 630 may define such openings 632 about the perimeter of the gasket/filter 622. When the gasket 610 is not compressed, the gasket 610 is not visible through the sheath openings 632. However, when the gasket 610 is compressed, the gasket 610 shifts with respect to the sheath 630 such that the gasket 610 is visible through the openings 632 in the sheath 630. Additionally or alternatively, the openings 632 may be substantially closed when the gasket 610 is not compressed but are opened as the gasket 610 is tightened or stretched about the body 602 such that the gasket 610 becomes visible as it is tightened or stretched. The transition from a first visual state, where the gasket 610 is not visible, to a second visual state, where the gasket 610 is visible, thus provides an indication of the seal state of the sterilization container 600. Accordingly, the gasket 610 and sheath 630 together form the seal indicator 616, and the first visual state may be referred to as the first indicator state and the second visual state may be referred to as the second indicator state. Further, in embodiments in which the sheath openings 632 are defined about the perimeter of the gasket/filter 622, the seal indicator 616 may be visible from all sides of the container 600, i.e., from both ends 602a, 602b and sides 602c, 602d of the body 602.

Similar to the other seal indicator embodiments described herein, it will be appreciated that the sheath 630 comprises a first indicium 616a and the gasket 610 comprises a second indicium 616b. The first indicium 616a may be a first color or hue and the second indicium 616b may be a second color or hue. The first and second colors/hues may be selected such that there is a high contrast between the colors/hues and/or between the colors/hues and the sterilization container 600, and/or the colors/hues may be selected to reinforce the signal communicated by the color or hue. For example, in an exemplary embodiment, the first color is red to indicate the container 300 is unsealed (i.e., contaminants could enter the container 600 and reach any articles in the interior 606), and the second color is green to indicate the container 600 is sealed (i.e., contaminants cannot enter the container 600 and any articles in the container 600 would remain sterile after sterilization). In another exemplary embodiment, the sheath 630 is the same color as the filter 620 of the combination gasket/filter 622 and, thus, the first color (i.e., the color of the sheath 630 and filter 620 and, therefore, the vast majority of the gasket/filter 622) may be a more subdued or aesthetically pleasing or calming color than red, such as blue. In such embodiments, the second color, i.e., the color of the gasket 610, may be a high contrast color with respect to blue, such as red. In any event, the seal indicator 616 is configured to display only the first color when the container 600 is unsealed and to display the second color when the container 600 is sealed, such that the seal indicator 616 indicates a change in the seal state of the container 600 through a change in color.

As further described herein, a change in state, i.e., from the first indicator state to the second indicator state or from the second indicator state to the first indicator state, may be achieved by a change in color, shape, size, position, etc. of the seal indicator 616 to signal the container 600 has transitioned from its unsealed state to its sealed state or from its sealed state to its unsealed state. Thus, when the gasket 610 is not compressed, or not fully compressed, such that the interior 606 is not sealed against the ingress of contaminants, the container 600 is in its first, unsealed state and the seal indicator 616 is in its first indicator state. Similarly, when the gasket 610 is fully compressed, such that the interior 606 is sealed against the ingress of contaminants, the container 600 is in its second, sealed state and the seal indicator 616 transitions from its first indicator state to its second indicator state. Other means for indicating the seal state of the container 600 or the integrity of the gasket 610, e.g., auditory or other non-visual indicators, may be used as well.

Additionally, each gasket assembly 612 includes means for tightening or stretching the gasket 610 to compress the gasket 610 against the body 602, thereby securing the gasket/filter 622 with respect to the body 602 such that the container interior 606 is sealed against the ingress of contaminants. The tightening or stretching means 634 can include any suitable mechanism for tightening the gasket 610 about the body 602. For instance, as illustrated most clearly in FIG. 15, the tightening or stretching means of the gasket assembly 612 may include a first end member 636 on a first end of a gasket 610 and a second end member 638 on a second end of the gasket 610. The first end member 636 defines a projection 640, and the second end member 638 defines a notch or opening 642 that is configured to receive the projection 640. As shown in FIG. 15, when the projection 640 is not received in the notch 642, the gasket 610 is loose, i.e., the gasket 610 is not compressed against the container body 602 and the container 600 is in its unsealed state. When the gasket/filter 622 is positioned on the body 602 and the projection 640 of the gasket assembly 612 is received in the notch 642, the second end of the gasket 610 is pulled to the first end of the gasket 610, and the gasket 610 is thereby tightened or stretched, i.e., the gasket 610 is compressed against the body 602 and the container 600 is in its sealed state. Further, as illustrated in FIG. 14, the body 602 may define grooves 601, and the gasket portion 610 of the combination gasket/filter 622 is received in a groove 601 as the gasket 610 is compressed against the body 602. The grooves 601 may help keep the gaskets 610 in position with respect to the body 602, e.g., by fitting within a groove 601, a gasket 610 is less likely to slip along the vertical direction V, which can help the gasket 610 initially be compressed as well as remain compressed against the body 602. The grooves 601 may provide other benefits as well, e.g., fitting into the grooves 601 as they are tightened or stretched may help the gaskets 610 transition from a position in which they are not seen through the openings 632 in the sheath 630 to a position in which the gaskets 610 are seen through the sheath openings 632.

It will be appreciated that the projection 640 and/or the notch 642 includes features for preventing the projection 640 from pulling out of the notch 642 once the projection 640 is inserted into the notch 642 to compress the gasket 610 against the body 602. For example, the projection 640 may have a triangular or wedge shape, where the thin or pointed end of the triangle or wedge is inserted into the notch 642 first, and the wider base of the triangle or wedge catches on the second end member 638 when the projection 640 is pushed or pulled on. Thus, the projection 640 cannot easily be removed from the notch 642. Additionally, in some embodiments, the projection 640 and notch 642 may be reversed, e.g., the first end member 636 may define the notch 642 and the second end member 638 may define the projection 640. Other suitable configurations of the tightening/stretching means 634 may be utilized as well.

As previously described, the exemplary sterilization container 600 comprises multiple gasket assemblies 612. Referring to FIG. 13, the tightening/stretching means 634 of each gasket assembly 612 are offset around the perimeter of the container 600. That is, the tightening/stretching means 634 of one gasket assembly 612 is positioned at a first location on the perimeter of the container 600, and the tightening/ stretching means 634 of another gasket assembly 612 is positioned at a second location of the perimeter of the container 600, where the second location is different from the first location. In the depicted embodiment, the second location is laterally spaced apart from the first location along the first side 602c of the body 602. Further, because each gasket 610 extends about the perimeter of the container 600, the gaskets 610 are vertically spaced apart from one another. Moreover, each tightening/stretching means 634, including the first and second end members 636, 638, protrudes through a vent opening 618 in the lid 604, which, in part, allows features such as tamper evidence to be incorporated into the sterilization container 600 and/or allows the projection 640 to be secured against retreat from the notch 642. As illustrated in FIG. 16, at least one projection 640 may define an aperture 644 therein, and a tag 646 may be positioned within the aperture 644. It will be appreciated that the tag 646 may be a tamper evidence tag configured to help a user to ascertain whether an attempt has been made to open the container 600 or whether the container 600 has been opened and resealed, either of which could possibly compromise the sterility of the contents of the container 600. Additionally or alternatively, the tag 646 may serve other purposes. For instance, the tag 646 may include a label that, e.g., specifies the contents of the container 600, the date and time of sterilization, and/or other pertinent information, or a way to access such information, such as a radio-frequency identification (RFID) tag, a barcode, a matrix or two-dimensional barcode (or Quick Response (QR) code), or other appropriate means for accessing such information.

Accordingly, the sterilization container 600 described with respect to FIGS. 13-16 provides improved sealing of the container interior 606, as well as an indicator for indicating the state of the seal, i.e., of the integrity of the seal, between the interfacing components. For instance, the container 600 utilizes a combination gasket/filter 622, i.e., a gasket and filter that are integrally formed as a single piece, which extends across the entire open top portion 608 of the body 602 to form a barrier against contamination of the container contents. The single piece gasket/filter completely covering the body 602 minimizes interfaces, thereby reducing opportunities for contaminants to breach the container interior 606. Moreover, the combination gasket/filter incorporates a seal indicator 616 to indicate to a user of the container 600 whether the interior 606 of the container 600 is sealed against the ingress of contaminants, which may indicate to the user that the sterility of the container 600 has been maintained post-sterilization. Of course, other benefits and advantages also may be realized from the subject matter discussed with respect to FIGS. 13-16.

The present subject matter also provides methods for indicating the integrity of a gasket of a sterilization container. For example, an exemplary method comprises providing a container body and a container lid that together define an interior for receipt of articles for sterilization. The container body has an open top portion, and the container lid covers the open top portion to close the sterilization container. The method also comprises providing a gasket that extends between the container body and the container lid when the container lid is positioned on the container body to seal the interior against an ingress of contaminants. Exemplary container bodies, lids, and gaskets are described with respect to the various sterilization container embodiments 300, 400, 500, 600 discussed herein.

Moreover, as described with respect to the sterilization container 600, in some embodiments a combination gasket/ filter and lid may be used to cover the open top portion of the body and thereby close the sterilization container. In such embodiments, the container interior may be defined by the container body and combination gasket/filter.

Further, the method comprises providing a seal indicator for indicating a seal state of the sterilization container. The seal indicator has a first indicium and a second indicium. The method also comprises displaying the first indicium when the sterilization container is in an unsealed state and displaying the second indicium when the sterilization container is in a sealed state. The seal indicator is visible to a user of the sterilization container such that the second indicium is not visible to the user in the unsealed state and the first indicium is not visible to the user in the sealed state. Moreover, in some embodiments, displaying the second indicium comprises displacing the seal indicator from a first position to a second position. Exemplary seal indicators are described with respect to the various sterilization container embodiments 300, 400, 500, 600 discussed herein. In addition, modifications or extensions of the exemplary method also may be realized from the sterilization container embodiments and other subject matter discussed herein.

Additionally, although not described above with respect to every sterilization container embodiment 300, 400, 500, 600, it will be appreciated that each sterilization container includes means for a sterilant to enter the container interior to sterilize any articles within the container. For example, vents or openings, as shown in the lids of the container embodiments 300, 400, 500, 600 (e.g., in FIGS. 1, 6, 7, and 9-16), allow fluids, including a sterilant such as steam or a chemical agent, to pass into the sterilization container to sterilize any articles within the container interior. Further, as described herein, the vents or openings allow fluids to pass from the container interior to the exterior, e.g., to help dry or aerate the articles as the sterilant evaporates or degases. As further described herein, the seal indicators may be configured such that the sterilization modality, including the sterilant used in the sterilization process, does not affect the seal indicator. For example, the sterilization modality does not cause the seal indicator to transition from displaying a first indicium to displaying a second indicium; as a particular example, the sterilization modality does not cause the seal indicator to change color. However, in some embodiments, the sterilization modality may help establish the seal between the container lid and container body and a portion of the sterilization process (such as elevated temperature or pressure) may cause the seal indicator to transition from one indicator state to another based on the establishment of the container seal. In such embodiments, the seal indicator may be indirectly affected by the sterilization modality, although the seal indicator does not transition between indicator states based solely on the sterilization modality but, rather, in response to the effect of the sterilization modality on the container seal.

Moreover, it will be appreciated that, although not described above with respect to every sterilization container embodiment 300, 400, 500, 600, the materials of each component of the container are selected to be compatible with the sterilization modality to which the container is subjected. For instance, the container body, container lid, and container gasket are each formed from a material that is compatible with the sterilization conditions to which the container will be submitted or vice versa, the sterilization conditions for a given container are selected to be within a range compatible with the material capabilities of the container materials. For example, the body and lid of each container 300, 400, 500, 600 can be reusable and can be formed from a rigid material such stainless steel, anodized aluminum, polyetheretherketone (PEEK), polyaryletherketone, polyphenylsulphone (PPSU), polysulphone (PSU), filled PPSU, and filled PSU. Once sealed, as described in greater detail herein, the container can then be transferred to sterilizing equipment and exposed to sterilization conditions as generally known in the art. Such sterilization conditions can include, for example, steam, ethylene oxide, or hydrogen peroxide plasma sterilization conditions. Sterilization conditions are the conditions present during a particular sterilization methodology utilized that substantially kills or completely destroys bacteria and other infectious organisms in an industrial or medical product to the desirable sterility assurance level (e.g., $\geq 10^{-6}$ log reduction for terminal sterilization). The compatibility of the container materials with the sterilization modality may be one way in which the seal indicator of the container is unaffected by the sterilization modality. That is, the seal indicator materials may be selected such that the indicator is not induced to transition between indicia based on the sterilization conditions but based on whether the seal between the lid and body is established or broken.

Also, although not described above with respect to every sterilization container embodiment 300, 400, 500, 600, it will be understood that one or more tags, such as tamper evidence tags and/or contents labels, may be included with each sterilization container. For example, a single use tamper evident tag, which breaks upon opening, may be attached to each sterilization container when the container is sealed. In one embodiment, a tamper evident tag includes a plastic flap across the interface between the container body and lid that tears upon opening. Additionally or alternatively, other tags or labels may be included with each sterilization container described herein. For instance, each container may include a label that, e.g., specifies the contents of the container, the date and time of sterilization, and/or other pertinent information, or a way to access such information, such as a radio-frequency identification (RFID) tag, a barcode, a matrix or two-dimensional barcode (or Quick Response (QR) code), or other appropriate means for accessing such information.

Further, it will be appreciated that the sterilization containers described herein may be configured to stack on top of one another or other containers. For example, the lids of the sterilization containers may provide rigidity, stability, and/or protection for the filter media such that the containers may be stacked. In addition, in embodiments similar to the sterilization containers 500 and 600, where the filter media is disposed between the lid and body and supports the lid at least in part, the edges of the filter media may be reinforced to provide rigidity for stacking. Moreover, the containers may include features for keeping space between the containers when stacked such that sterilant and/or evaporating fluids can enter and/or exit the containers through the vents. That is, the containers may be configured such that the vents are not blocked when one container is stacked on top of another.

Additionally, the sterilization containers described herein may include a second lid or cover that fits over the lids described herein, e.g., to prevent intrusions through the vent openings defined in the top of the lid. For example, it will be appreciated that contaminants or other debris matter could fall through the vent openings illustrated in the exemplary embodiments of the present subject matter, and such contaminants could fall into the container via a compromised filter or when the container is opened, thus compromising the sterility of the articles within the container. A particular example, an instrument end or the like could enter the vent openings, e.g., if the instrument is dropped on the lid, and thereby pierce, puncture, cut, tear, etc. the filter media that is positioned between the vent openings and the container interior, which could compromise the integrity of the filter and thereby could compromise the sterility of the articles within the container. Therefore, a second lid or cover may be provided to shield the vent openings defined in the exemplary lids described herein. The second lid or cover may be releasably attached to the lid or may be durably attached to the lid. Further, the second lid or cover may itself have define openings therein for fluids, such as the sterilant of the selected sterilization modality, to enter and exit the container. The defined openings of the second lid or cover are judiciously shaped and sized to ensure the desired Volume to Vent (V-to-V) ratio is maintained. It will be appreciated that such openings may be defined in the second lid or cover such that such openings do not face the same breach potential as the vent openings in the underlying lid. Alternatively or additionally, a gap may be defined between the second lid or cover and the underlying lid, e.g., around the outer perimeter of the lid, such that fluids may enter and exit the container via the gap between the lid and the second lid or cover. The second lid or cover may have other configurations as well, and in some embodiments, such a protective lid or cover may be unnecessary or undesirable and, thus, may be omitted.

This written description uses examples to disclose the invention, including the best mode, and also to enable any person skilled in the art to practice the invention, including making and using any devices or systems and performing any incorporated methods. The patentable scope of the invention is defined by the claims and may include other examples that occur to those skilled in the art. Such other examples are intended to be within the scope of the claims if they include structural elements that do not differ from the literal language of the claims or if they include equivalent structural elements with insubstantial differences from the literal language of the claims.

What is claimed is:

1. A sterilization container, comprising:
 a body including a first end, a second end opposite the first end, a first side extending between the first and second ends, and a second side opposite the first side and extending between the first and second ends, the body further including an open top portion;
 a lid, the body and lid together defining an interior;
 a closure mechanism comprising a latch assembly that includes a first arm attached to the lid and pivotable with respect to the lid, a second arm attached to the lid and pivotable with respect to the lid, a pair of first hooks extending form the first arm to the body, and a pair of second hooks extending from the second arm to the body, the latch assembly further includes a pair of end latches, a first end latch of the pair of end latches attached to the first arm and a second end latch of the pair of end latches attached to the second arm, wherein the first end latch engages a first end catch on the first end of the body, wherein the second end latch engages a second end catch on the second end of the body; and
 a gasket for sealing the interior against an ingress of contaminants,
 wherein the closure mechanism compresses the gasket between the lid and the body to seal the interior against the ingress of contaminants.

2. The sterilization container of claim 1, further comprising:
   a filter extending across the open top portion of the body from the first end to the second end and from the first side to the second side,
   wherein the gasket and filter are integrally formed as a single piece gasket/filter.

3. The sterilization container of claim 1, further comprising:
   a seal indicator for indicating a seal state of the sterilization container, the seal indicator having a first indicator state that indicates an unsealed container state and a second indicator state that indicates a sealed container state,
   wherein the seal indicator is in the first indicator state when the gasket is not compressed to seal the sterilization container against the ingress of contaminants, and
   wherein the seal indicator is in the second indicator state when the gasket is compressed to seal the sterilization container against the ingress of contaminants.

4. The sterilization container of claim 3, wherein the seal indicator displays a first indicium in the first indicator state and a second indicium in the second indicator state, and
   wherein the first indicium is a first color and the second indicium is a second color such that the seal indicator indicates a change in the seal state of the sterilization container through a change in color.

5. The sterilization container of claim 3,
   wherein the seal indicator is visible from each of the first end, the second end, the first side, and the second side.

6. The sterilization container of claim 1, wherein the gasket extends between the body and the lid to seal the interior against the ingress of contaminants.

7. The sterilization container of claim 6, wherein the gasket extends about a perimeter of the body and the lid.

8. The sterilization container of claim 1, wherein the lid includes a first end, a second end opposite the first end, a first side extending between the first and second ends, and a second side opposite the first side and extending between the first and second ends,
   wherein the lid defines a groove for receipt of each of the first arm and the second arm, and
   wherein the groove is defined inward of each of the first and second ends and first and second sides of the lid such that the groove is offset from each of the first and second ends and first and second sides of the lid.

9. The sterilization container of claim 1, wherein the lid includes an outer edge,
   wherein the lid defines a recess around the outer edge that has a shape complementary to both the first arm and the second arm for receipt of the first and second arms.

10. The sterilization container of claim 1, wherein the closure mechanism comprises more than two latch assemblies disposed around the perimeter of the lid.

11. The sterilization container of claim 1, further comprising:
    a body interface feature along a rim at the open top portion of the body; and
    a lid interface feature along an outer edge of the lid,
    wherein each of the body interface feature and the lid interface feature defines a series of channels such that the body interface feature meshes with the lid interface feature to form a tortuous path from an environment external to the container to the interior of the container.

12. The sterilization container of claim 1, wherein the closure mechanism comprises a plurality of latch assemblies, each latch assembly including an arm that extends downward from the lid toward the body, each arm including a projection that extends inward toward the body from a distal end of the arm, and
    wherein each projection is configured to engage a lip defined along the open top portion of the body to secure the lid to the body.

13. The sterilization container of claim 1, further comprising:
    a filter extending across the open top portion of the body from the first end to the second end and from the first side to the second side,
    wherein the gasket and filter are integrally formed as a single piece gasket/filter,
    wherein the closure mechanism further comprises a plurality of gasket assemblies that comprise the gasket of the gasket/filter, and
    wherein the gasket/filter covers the open top portion of the body and the gasket assemblies compress the filter of the gasket/filter against the body to close and seal the interior.

14. A sterilization container, comprising:
    a body including a first end, a second end opposite the first end, a first side extending between the first and second ends, and a second side opposite the first side and extending between the first and second ends, the body further including an open top portion;
    a lid, the body and lid together defining an interior;
    a filter extending across the open top portion of the body from the first end to the second end and from the first side to the second side;
    a gasket for sealing the interior against an ingress of contaminants, wherein the gasket and filter are integrally formed as a single piece gasket/filter; and
    a closure mechanism comprising a plurality of gasket assemblies that comprise the gasket of the gasket/filter, wherein the gasket/filter covers the open top portion of the body and the gasket assemblies compress the filter of the gasket/filter against the body to close and seal the interior,
    wherein the closure mechanism compresses the gasket between the lid and the body to seal the interior against the ingress of contaminants.

\* \* \* \* \*